(12) United States Patent
Jackson

(10) Patent No.: US 8,938,826 B2
(45) Date of Patent: *Jan. 27, 2015

(54) PATIENT POSITIONING SUPPORT STRUCTURE

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 13/902,455

(22) Filed: May 24, 2013

(65) Prior Publication Data

US 2013/0318718 A1    Dec. 5, 2013

Related U.S. Application Data

(63) Continuation-in-part of application No. 13/317,012, filed on Oct. 6, 2011, now Pat. No. 8,719,979, which is a continuation of application No. 12/460,702, filed on Jul. 23, 2009, now Pat. No. 8,060,960, which is a continuation of application No. 11/788,513, filed on Apr. 20, 2007, now Pat. No. 7,565,708, which is a continuation-in-part of application No. 11/159,494, filed on Jun. 23, 2005, now Pat. No. 7,343,635, which is a continuation-in-part of application No. 11/062,775, filed on Feb. 22, 2005, now Pat. No. 7,152,261.

(60) Provisional application No. 60/798,288, filed on May 5, 2006.

(51) Int. Cl.
| | |
|---|---|
| *A61G 13/04* | (2006.01) |
| *A61G 13/08* | (2006.01) |
| *A61G 13/02* | (2006.01) |
| *A61G 7/00* | (2006.01) |
| *A61G 7/008* | (2006.01) |
| *A61G 13/00* | (2006.01) |
| *A61B 6/04* | (2006.01) |
| *A61G 13/06* | (2006.01) |

(52) U.S. Cl.
CPC ............... *A61G 13/02* (2013.01); *A61G 7/001* (2013.01); *A61G 7/008* (2013.01); *A61G 13/0036* (2013.01); *A61G 13/04* (2013.01); *A61G 13/08* (2013.01); *A61B 6/0407* (2013.01); *A61G 13/06* (2013.01); *A61G 2013/0054* (2013.01)
USPC ........................... 5/611; 5/610; 5/607; 5/613

(58) Field of Classification Search
USPC .............. 5/607, 608, 610, 611, 613, 617, 618
See application file for complete search history.

(56) References Cited

U.S. PATENT DOCUMENTS

| | | |
|---|---|---|
| 1,171,713 A | 2/1916 | Gilkerson |
| 1,667,982 A | 5/1928 | Pearson |

(Continued)

FOREIGN PATENT DOCUMENTS

| | | |
|---|---|---|
| GB | 569758 | 6/1945 |
| GB | 810956 | 3/1959 |

(Continued)

OTHER PUBLICATIONS

Complaint for Patent Infringement, *Jackson v. Mizuho Orthopedic Sys., Inc.*, No. 4:12-CV-01031 (W.D. Mo. Aug. 7, 2012).

(Continued)

*Primary Examiner* — Michael Trettel
(74) *Attorney, Agent, or Firm* — Polsinelli PC

(57) ABSTRACT

A patient support system includes independently adjustable columns supporting a hinged bending or breaking patient support structure. At least one column includes at least two sections. A coordinated drive system provides for upwardly breaking and downwardly breaking orientations of the two sections in various inclined and tilted positions.

26 Claims, 23 Drawing Sheets

(56) References Cited

U.S. PATENT DOCUMENTS

| | | | |
|---|---|---|---|
| 1,799,692 A | | 4/1931 | Knott |
| 1,938,006 A | | 12/1933 | Blanchard |
| 2,261,297 A | | 11/1941 | Seib |
| 2,475,003 A | | 7/1949 | Black |
| 2,636,793 A | * | 4/1953 | Meyer ............................. 5/618 |
| 3,046,071 A | | 7/1962 | Shampaine et al. |
| 3,281,141 A | | 10/1966 | Smiley et al. |
| 3,584,321 A | * | 6/1971 | Buchanan ........................ 5/601 |
| 3,599,964 A | | 8/1971 | Magni |
| 3,766,384 A | | 10/1973 | Anderson |
| 3,814,414 A | | 6/1974 | Chapa |
| 3,832,742 A | | 9/1974 | Stryker |
| 4,101,120 A | | 7/1978 | Seshima |
| 4,131,802 A | | 12/1978 | Braden et al. |
| 4,144,880 A | | 3/1979 | Daniels |
| 4,148,472 A | | 4/1979 | Rais et al. |
| 4,175,550 A | | 11/1979 | Leininger et al. |
| 4,186,917 A | | 2/1980 | Rais et al. |
| 4,227,269 A | | 10/1980 | Johnston |
| 4,230,100 A | | 10/1980 | Moon |
| 4,474,364 A | | 10/1984 | Brendgord |
| 4,503,844 A | | 3/1985 | Siczek |
| 4,552,346 A | | 11/1985 | Schnelle et al. |
| 4,712,781 A | | 12/1987 | Watanabe |
| 4,718,077 A | | 1/1988 | Moore et al. |
| 4,763,643 A | | 8/1988 | Vrzalik |
| 4,872,657 A | | 10/1989 | Lussi |
| 4,937,901 A | | 7/1990 | Brennan |
| 4,970,737 A | | 11/1990 | Sagel |
| 5,088,706 A | | 2/1992 | Jackson |
| 5,131,106 A | * | 7/1992 | Jackson ............................ 5/613 |
| 5,208,928 A | | 5/1993 | Kuck et al. |
| 5,210,888 A | | 5/1993 | Canfield |
| 5,231,741 A | | 8/1993 | Maguire |
| 5,239,716 A | | 8/1993 | Fisk |
| 5,393,018 A | | 2/1995 | Roth et al. |
| 5,444,882 A | | 8/1995 | Andrews et al. |
| 5,461,740 A | * | 10/1995 | Pearson ............................ 5/611 |
| 5,468,216 A | | 11/1995 | Johnson et al. |
| 5,579,550 A | | 12/1996 | Bathrick et al. |
| 5,588,705 A | | 12/1996 | Chang |
| 5,613,254 A | | 3/1997 | Clayman et al. |
| 5,640,730 A | | 6/1997 | Godette |
| 5,658,315 A | | 8/1997 | Lamb et al. |
| 5,659,909 A | | 8/1997 | Pfeuffer et al. |
| 5,774,914 A | | 7/1998 | Johnson et al. |
| 5,794,286 A | | 8/1998 | Scott et al. |
| 5,862,549 A | | 1/1999 | Morton et al. |
| 5,870,784 A | | 2/1999 | Elliott |
| 6,000,076 A | | 12/1999 | Webster et al. |
| 6,260,220 B1 | * | 7/2001 | Lamb et al. ..................... 5/607 |
| 6,286,164 B1 | | 9/2001 | Lamb et al. |
| 6,295,671 B1 | | 10/2001 | Reesby et al. |
| 6,438,777 B1 | | 8/2002 | Bender |
| 6,499,162 B1 | | 12/2002 | Lu |
| 6,505,365 B1 | | 1/2003 | Hanson et al. |
| 6,526,610 B1 | | 3/2003 | Hand et al. |
| 6,634,043 B2 | | 10/2003 | Lamb et al. |
| 6,638,299 B2 | | 10/2003 | Cox |
| 6,681,423 B2 | | 1/2004 | Zachrisson |
| 6,701,553 B1 | | 3/2004 | Hand et al. |
| 6,971,131 B2 | | 12/2005 | Bannister |
| 6,971,997 B1 | | 12/2005 | Ryan et al. |
| 7,003,828 B2 | | 2/2006 | Roussy |
| 7,055,195 B2 | | 6/2006 | Roussy |
| 7,089,612 B2 | | 8/2006 | Rocher et al. |
| 7,103,931 B2 | | 9/2006 | Somasundaram et al. |
| 7,137,160 B2 | | 11/2006 | Hand et al. |
| 7,152,261 B2 | | 12/2006 | Jackson |
| 7,171,709 B2 | | 2/2007 | Weismiller |
| 7,234,180 B2 | | 6/2007 | Horton et al. |
| 7,331,557 B2 | | 2/2008 | Dewert |
| 7,343,635 B2 | | 3/2008 | Jackson |
| 7,565,708 B2 | | 7/2009 | Jackson |
| 7,596,820 B2 | | 10/2009 | Nielsen et al. |
| 7,739,762 B2 | * | 6/2010 | Lamb et al. ..................... 5/618 |
| 8,060,960 B2 | | 11/2011 | Jackson |
| 8,707,484 B2 | | 4/2014 | Jackson et al. |
| 8,719,979 B2 | | 5/2014 | Jackson |
| 2001/0037524 A1 | | 11/2001 | Truwit |
| 2004/0098804 A1 | | 5/2004 | Varadharajulu et al. |
| 2004/0133983 A1 | * | 7/2004 | Newkirk et al. ................. 5/624 |
| 2006/0123546 A1 | | 6/2006 | Horton et al. |
| 2006/0185090 A1 | | 8/2006 | Jackson |
| 2007/0107126 A1 | | 5/2007 | Koch et al. |
| 2007/0192960 A1 | | 8/2007 | Jackson |
| 2008/0000028 A1 | * | 1/2008 | Lemire et al. .................... 5/618 |
| 2008/0127419 A1 | | 6/2008 | Jensen |
| 2011/0107516 A1 | | 5/2011 | Jackson |
| 2011/0107517 A1 | | 5/2011 | Lamb et al. |
| 2012/0246829 A1 | | 10/2012 | Lamb et al. |
| 2012/0255122 A1 | | 10/2012 | Diel et al. |
| 2013/0254995 A1 | * | 10/2013 | Jackson ............................ 5/607 |

FOREIGN PATENT DOCUMENTS

| | | |
|---|---|---|
| JP | S53763 | 1/1978 |
| JP | 2000-060995 | 2/2000 |
| WO | WO99/07320 | 2/1999 |
| WO | WO00/62731 | 10/2000 |
| WO | WO01/60308 | 8/2001 |
| WO | WO03/070145 | 8/2003 |
| WO | WO2009/054969 | 4/2009 |
| WO | WO2009/100692 | 8/2009 |

OTHER PUBLICATIONS

First Amended Complaint for Patent Infringement And Correction Of Inventorship, *Jackson* v. *Mizuho Orthopedic Sys., Inc.*, No. 4:12-CV-01031 (W.D. Mo. Sep. 21, 2012).

Defendant Mizuho Orthopedic Systems, Inc.'s Answer To First Amended Complaint And Counterclaims, *Jackson* v. *Mizuho Orthopedic Sys., Inc.*, No. 4:12-CV-01031 (W.D. Mo, Nov. 1, 2012).

Plaintiff Roger P. Jackson, MD's, Reply To Counterclaims, *Jackson* v. *Mizuho Orthopedic Sys., Inc.*, No. 4:12-CV-01031 (W.D. Mo. Nov. 26, 2012).

Roger P. Jackson's Disclosure Of Asserted Claims And Preliminary Infringement Contentions, *Jackson* v. *Mizuho Orthopedic Sys., Inc.*, No. 4:12-CV-01031 (W.D. Mo. Jan. 4, 2013).

Second Amended Complaint For Patent Infringement, For Correction Of Inventorship, For Breach Of A Non-Disclosure And Confidentiality Agreement, And For Misappropriation Of Dr. Jackson's Right Of Publicity, *Jackson* v. *Mizuho Orthopedic Sys., Inc.*, No. 4:12-CV-01031 (W.D. Mo. Jan. 28, 2013).

Defendant Mizuho Orthopedic Systems, Inc.'s Answer To Second Amended Complaint And Counterclaims, *Jackson* v. *Mizuho Orthopedic Sys., Inc.*, No. 4:12-CV-01031 (W.D. Mo. Feb. 19, 2013).

Defendant Mizuho Osi's Invalidity Contentions Pursuant To The Parties' Joint Scheduling Order, *Jackson* v. *Mizuho Orthopedic Sys., Inc.*, No. 4:12-CV-01031 (W.D. Mo, Feb. 22, 2013).

Plaintiff Roger P. Jackson, Md's, Reply To Second Counterclaims, *Jackson* v. *Mizuho Orthopedic Sys., Inc.*, No. 4:12-CV-01031 (W.D. Mo. Mar. 12, 2013).

Roger P. Jackson, MD's Disclosure Of Proposed Terms To Be Construed, *Jackson* v. *Mizuho Orthopedic Sys., Inc.*, No. 4:12-CV-01031 (W.D. Mo. Apr. 5, 2013).

Defendant Mizuho Orthopedic Systems, Inc.'s Disclosure of Proposed Terms and Claim Elements for Construction, *Jackson* v. *Mizuho Orthopedic Sys., Inc.*, No. 4:12-CV-01031 (W.D. Mo. Apr. 5, 2013).

Mizuho Orthopedic Systems, Inc.'s Disclosure Of Proposed Claim Constructions And Extrinsic Evidence, *Jackson* v. *Mizuho Orthopedic Sys., Inc.*, No. 4:12-CV-01031 (W.D. Mo. May 13, 2013).

Plaintiff Roger P. Jackson, MD's Disclosure Of Preliminary Proposed Claim Constructions, *Jackson* v. *Mizuho Orthopedic Sys., Inc.*, No. 4:12-CV-01031 (W.D. Mo. May 13, 2013).

Defendant Mizuho Osi's Amended Invalidity Contentions Pursuant To The Parties' Joint Scheduling Order, *Jackson* v. *Mizuho Orthopedic Sys., Inc.*, No. 4:12-CV-01031 (W.D. Mo. May 15, 2013).

(56) References Cited

OTHER PUBLICATIONS

Joint Claim Construction Chart And Joint Prehearing Statement, *Jackson* v. *Mizuho Orthopedic Sys., Inc.*, No. 4:12-CV-01031 (W.D. Mo. Jun. 7, 2013).

Defendant Mizuho Orthopedic Systems, Inc.'s Objections And Responses To Plaintiff's First Set Of Interrogatories, *Jackson* v. *Mizuho Orthopedic Sys., Inc.*, No. 4:12-CV-01031 (W.D. Mo. Jun. 24, 2013).

Defendant Mizuho Orthopedic Systems, Inc.'s Opening Claim Construction Brief, *Jackson* v. *Mizuho Orthopedic Sys., Inc.*, No. 4:12-CV-01031 (W.D. Mo. Jul. 31, 2013).

Plaintiff Roger P. Jackson, MD's Opening Claim Construction Brief, *Jackson* v. *Mizuho Orthopedic Sys., Inc.*, No. 4:12-CV-01031 (W.D. Mo. Jul. 31, 2013).

Appendix A Amended Infringement Contentions Claim Chart For Mizuho's Axis System Compared To U.S. Patent No. 7,565,708, *Jackson* v. *Mizuho Orthopedic Sys., Inc.*, No. 4:12-CV-01031 (W.D. Mo. Aug. 12, 2013).

Appendix B Amended Infringement Contentions Claim Chart For Mizuho's Axis System Compared To U.S. Patent No. 8,060,960, *Jackson* v. *Mizuho Orthopedic Sys., Inc.*, No. 4:12-CV-01031 (W.D. Mo. Aug. 12, 2013).

Appendix C Amended Infringement Contentions Claim Chart For Mizuho's Proaxis System Compared To U.S. Patent No. 7,565,708, *Jackson* v. *Mizuho Orthopedic Sys., Inc.*, No. 4:12-CV-01031 (W.D. Mo. Aug. 12, 2013).

Appendix D Amended Infringement Contentions Claim Chart For Mizuho's Proaxis System Compared To U.S. Patent No. 8,060,960, *Jackson* v. *Mizuho Orthopedic Sys., Inc.*, No. 4:12-CV-01031 (W.D. Mo. Aug. 12, 2013).

Plaintiff Roger P. Jackson, MD's Responsive Claim Construction Brief, *Jackson* v. *Mizuho Orthopedic Sys., Inc.*, No. 4:12-CV-01031 (W.D. Mo. Aug. 16, 2013).

Defendant Mizuho Orthopedic Systems, Inc's Brief In Response To Plaintiff's Opening Claim Construction Brief, *Jackson* v. *Mizuho Orthopedic Sys., Inc.*, No. 4:12-CV-01031 (W.D. Mo. Aug. 16, 2013).

Plaintiff Roger P. Jackson, Md's Suggestions In Support Of His Motion To Strike Exhibit A Of Mizuho's Opening Claim Construction Brief, *Jackson* v. *Mizuho Orthopedic Sys., Inc.*, No. 4:12-CV-01031 (W.D. Mo. Aug. 16, 2013).

Defendant Mizuho Orthopedic Systems, Inc.'s Opposition To Plaintiff's Motion To Strike, *Jackson* v. *Mizuho Orthopedic Sys., Inc.*, No. 4:12-CV-01031 (W.D. Mo. Sep. 3, 2013).

Transcript of Claim Construction Hearing, *Jackson* v. *Mizuho Orthopedic Sys., Inc.*, No. 4:12-CV-01031 (W.D. Mo. Oct. 11, 2013).

Plaintiff Roger P. Jackson, MD's Claim Construction Presentation for U.S. District Judge Nanette K. Laughrey, *Jackson* v. *Mizuho Orthopedic Sys., Inc.*, No. 4:12-CV-01031 (W.D. Mo. Oct. 11, 2013).

Mizuho's Claim Construction Argument, *Jackson* v. *Mizuho Orthopedic Sys., Inc.*, No. 4:12-CV-01031 (W.D. Mo. Oct. 11, 2013).

Order, *Jackson* v. *Mizuho Orthopedic Sys., Inc.*, No. 4:12-CV-01031 (W.D. Mo. Apr. 4, 2014).

Brochure of OSI on Modular Table System 90D, pp. 1-15, date of first publication: Unknown.

Brochure of Smith & Nephew on Spinal Positioning System, 2003, 2004.

Pages from website http://www.schaerermayfieldusa.com, pp. 1-5, date of first publication: Unknown.

\* cited by examiner

Fig-1.

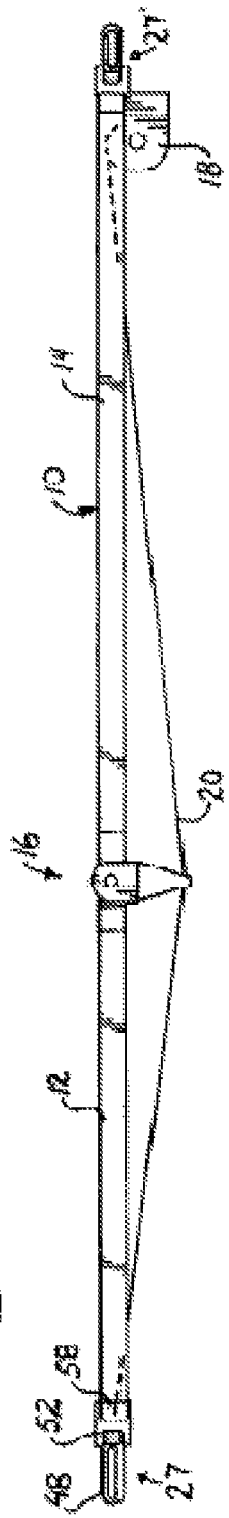
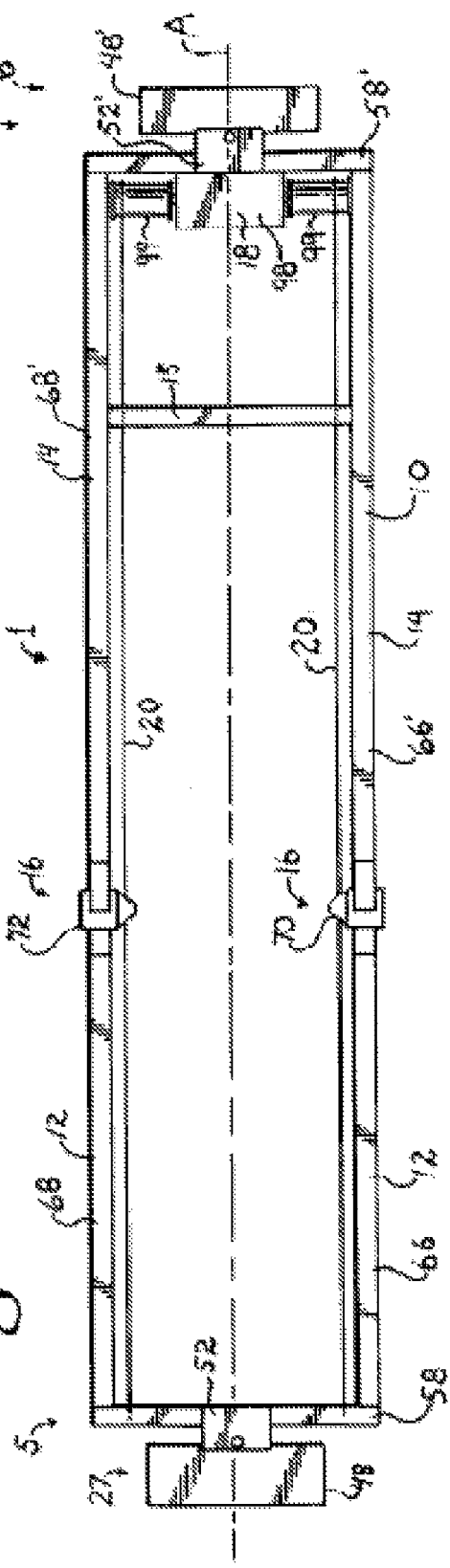

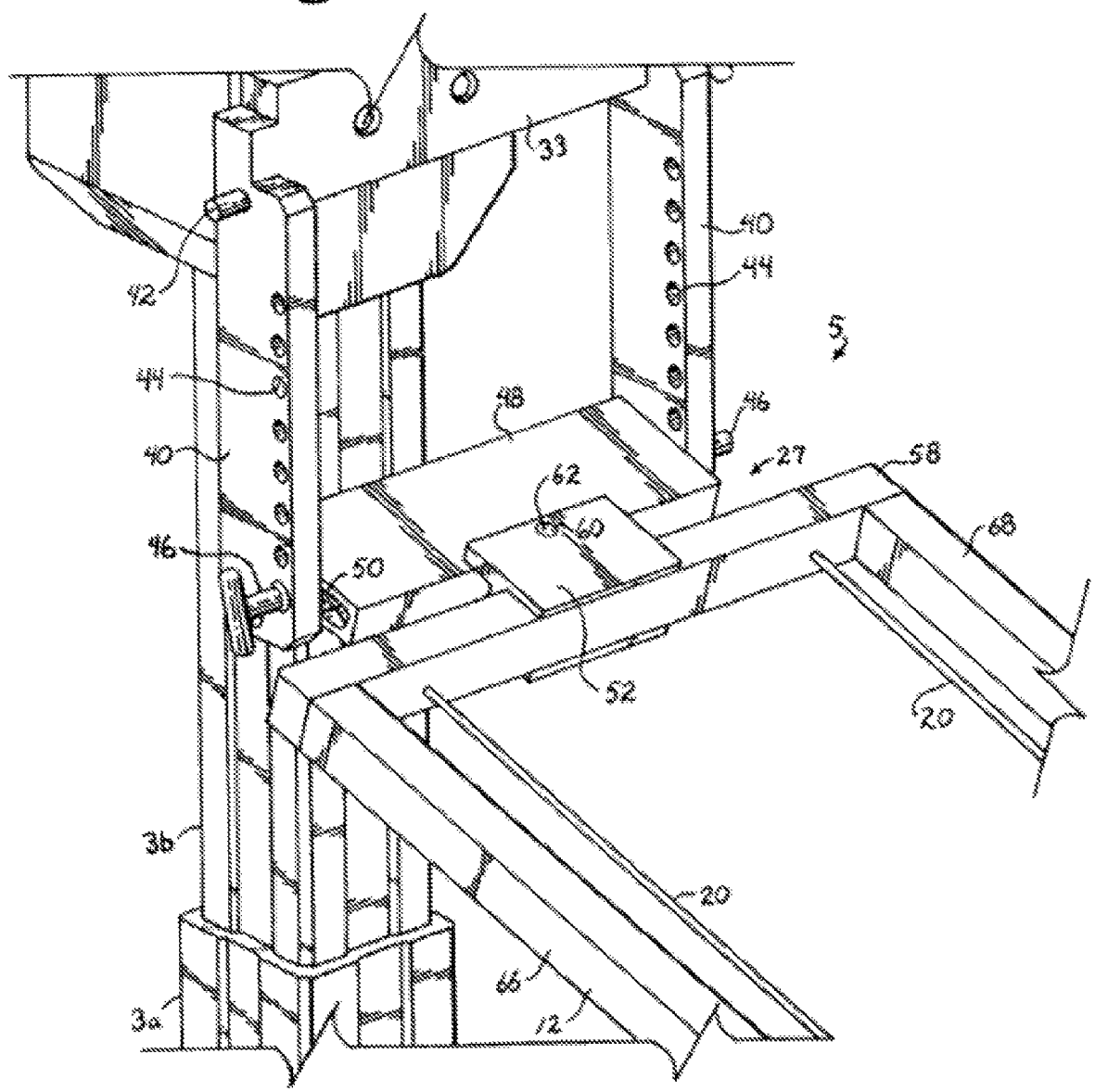

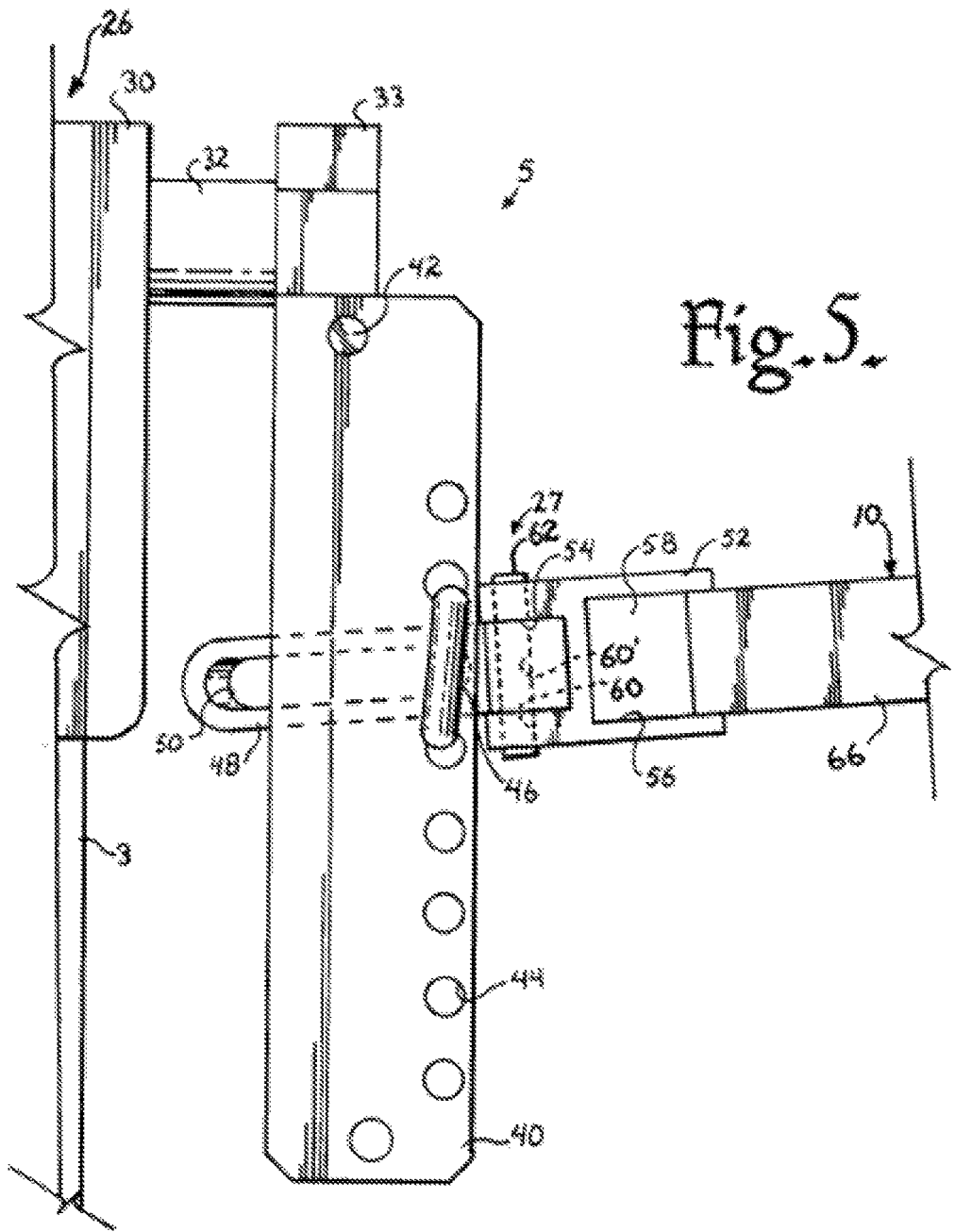

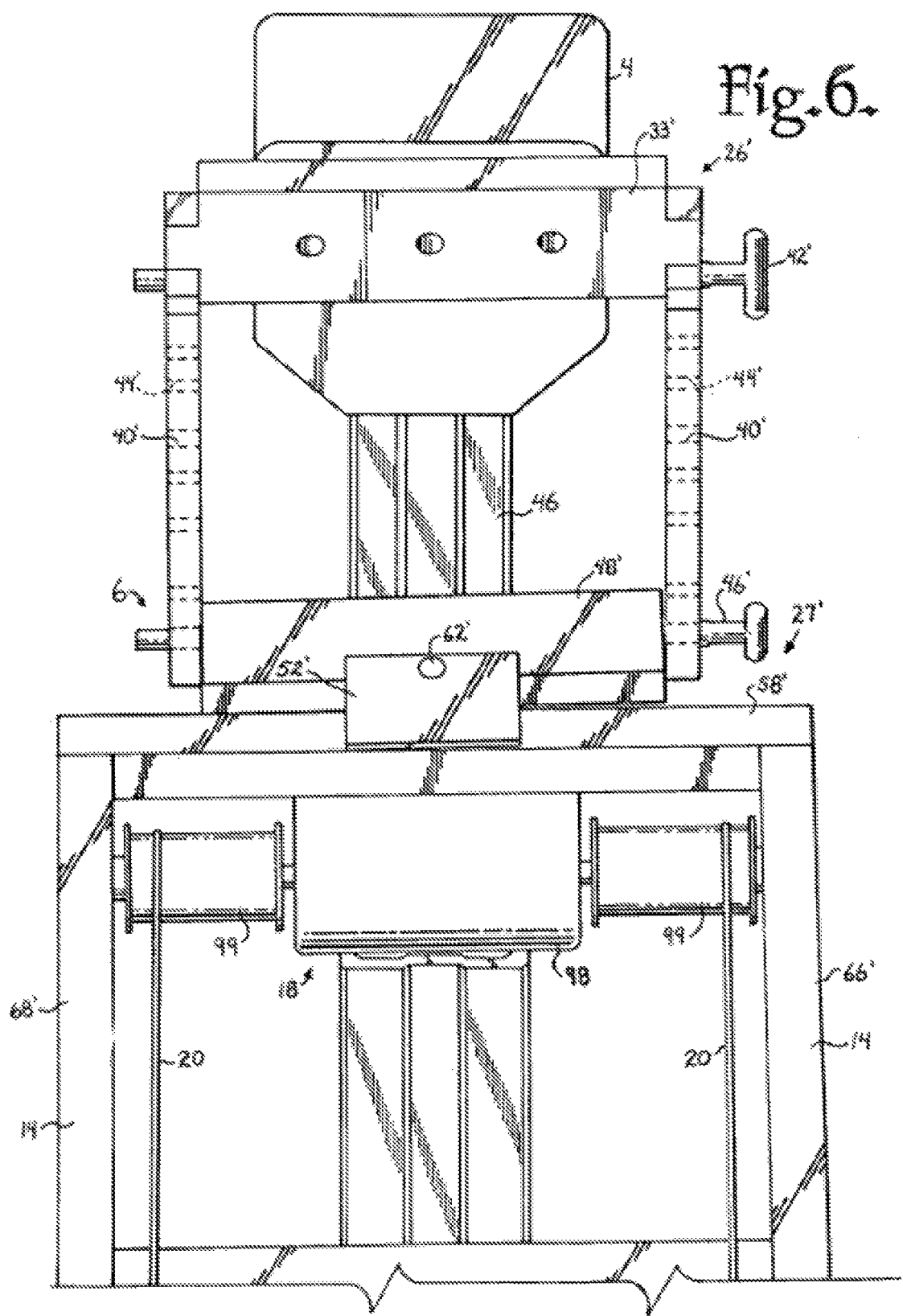

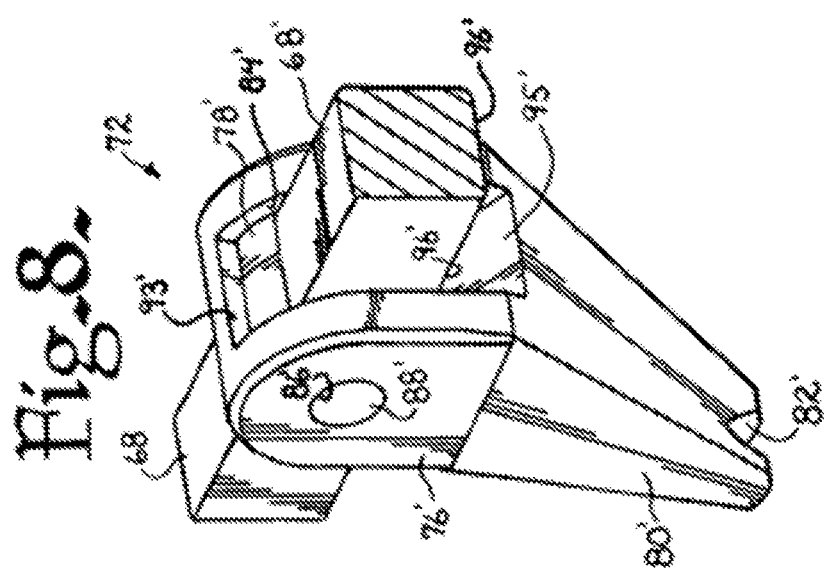
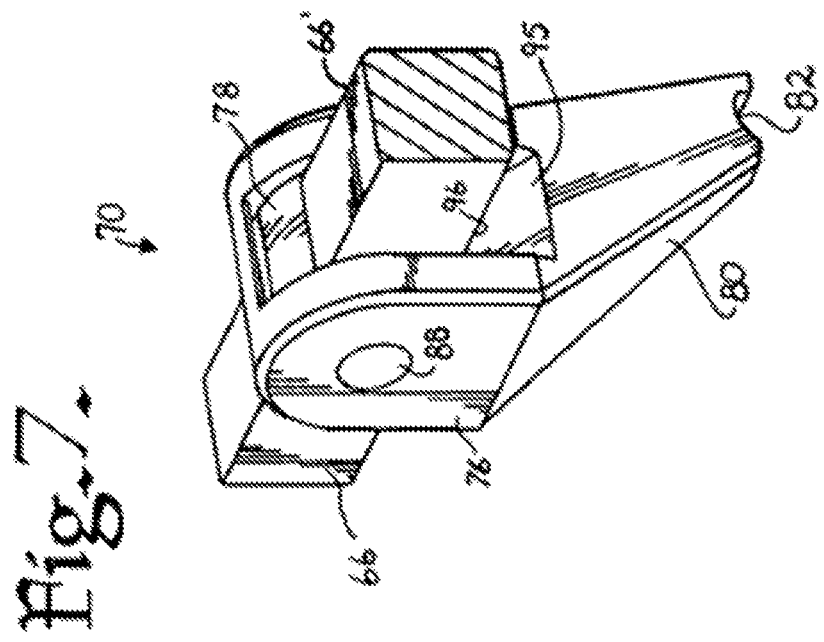

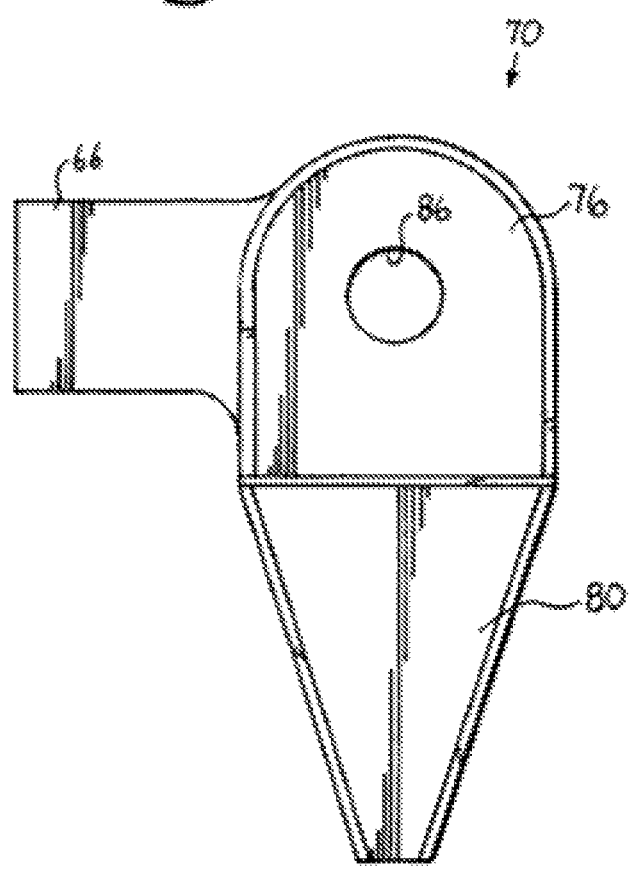

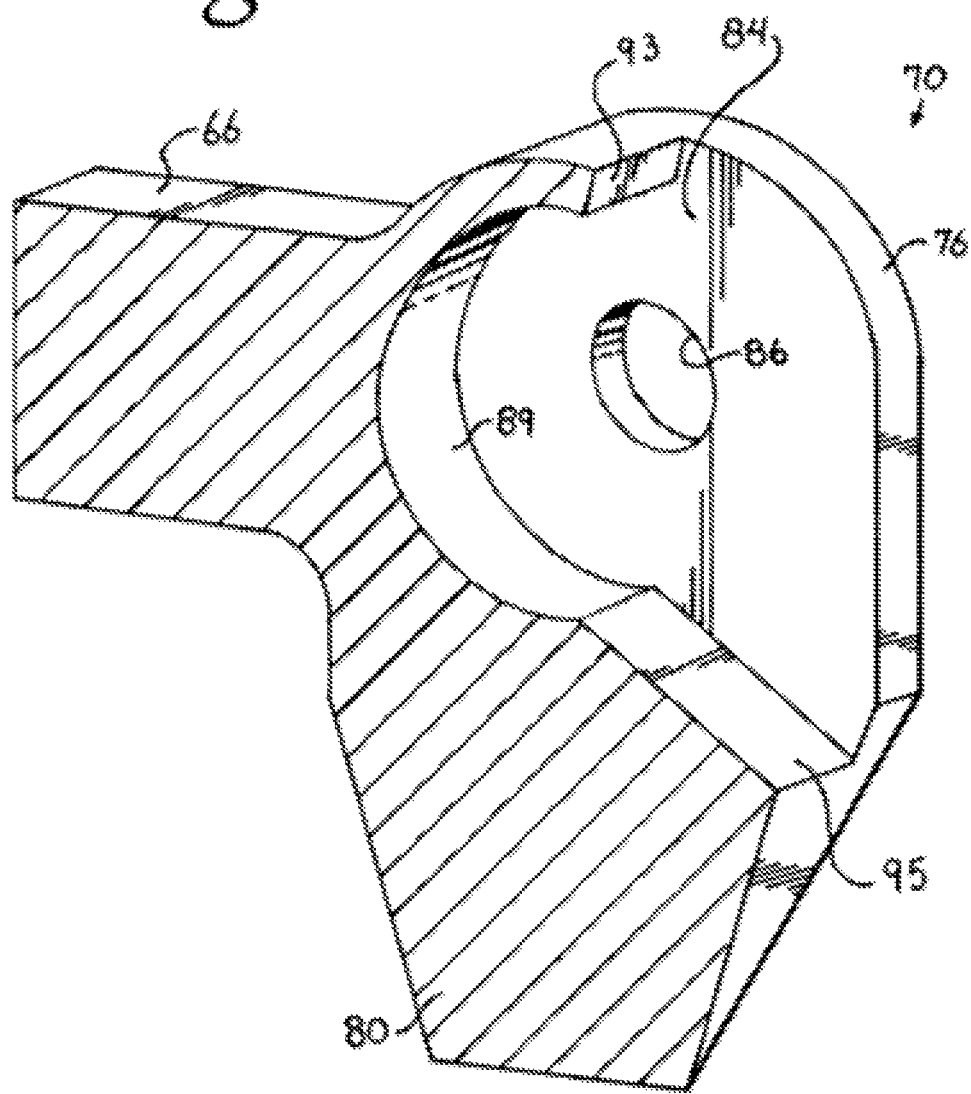

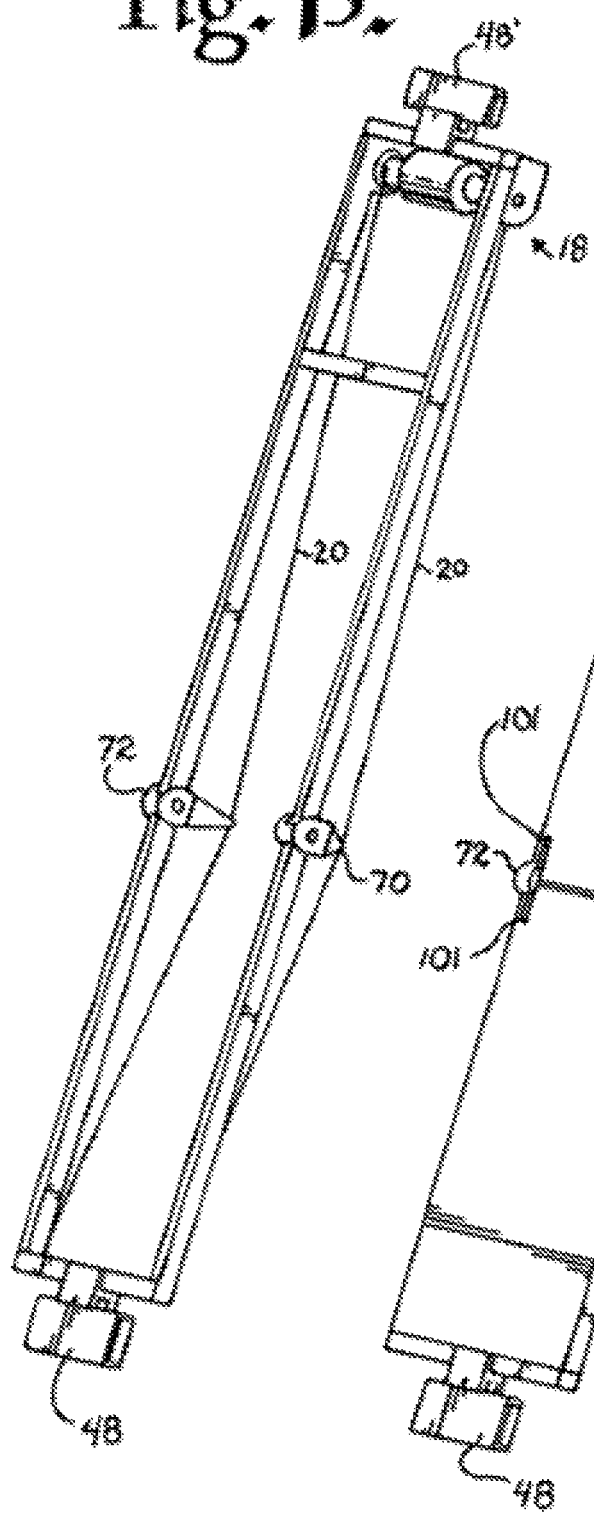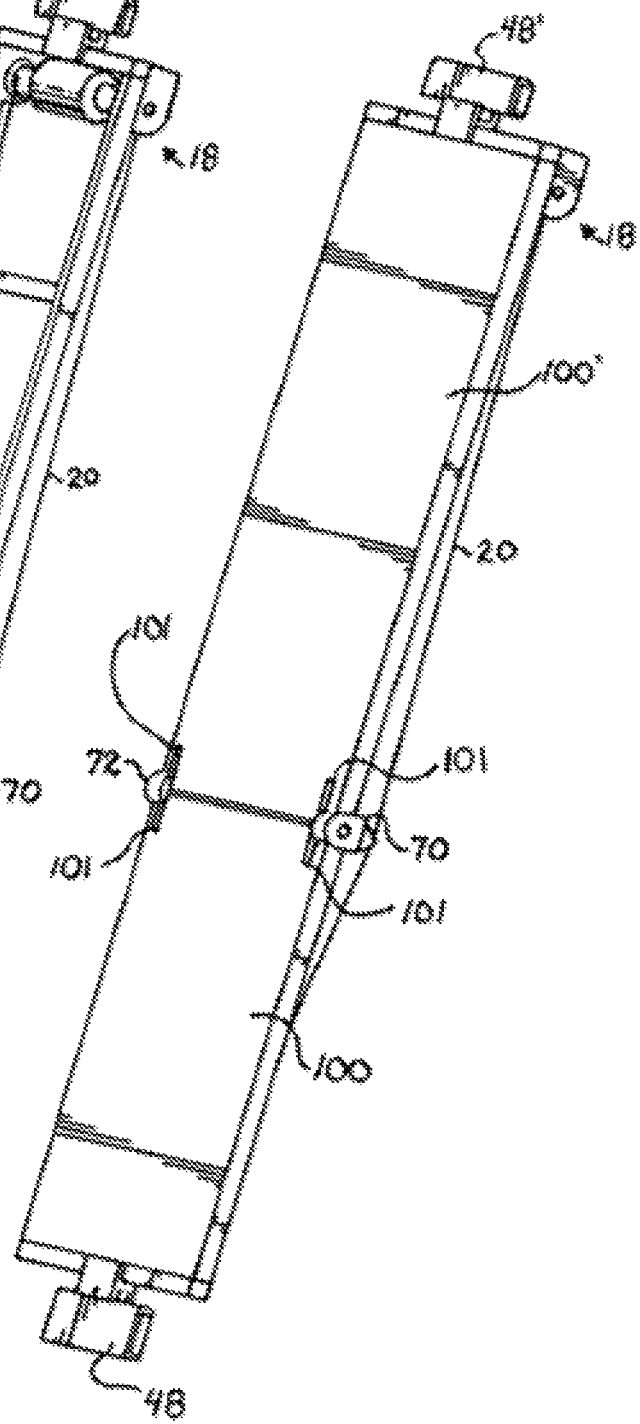

PATIENT POSITIONING SUPPORT STRUCTURE

CROSS-REFERENCE TO RELATED APPLICATIONS

This application is a continuation-in-part of U.S. application Ser. No. 13/317,012 filed Oct. 6, 2011, now U.S. Pat. No. 8,719,979, entitled Patient Positioning Support Structure, which application is a continuation of U.S. Ser. No. 12/460,702, filed Jul. 23, 2009, now U.S. Pat. No. 8,060,960, which is a continuation of U.S. Ser. No. 11/788,513, filed Apr. 20, 2007, now U.S. Pat. No. 7,565,708, which claims the benefit of U.S. Provisional Application No. 60/798,288 filed May 5, 2006 and is also a continuation-in-part of U.S. patent application Ser. No. 11/159,494 filed Jun. 23, 2005, now U.S. Pat. No. 7,343,635, which is a continuation-in-part of U.S. patent application Ser. No. 11/062,775 filed Feb. 22, 2005, now U.S. Pat. No. 7,152,261. The disclosures of all the preceding applications and patents are incorporated by reference herein.

BACKGROUND OF THE INVENTION

The present invention is directed to structure for use in maintaining a patient in a desired position during examination and treatment, including medical procedures such as imaging and surgery and in particular to such a structure that allows a surgeon to selectively position the patient for convenient access to the surgery site and providing for manipulation of the patient during surgery including the tilting, pivoting, angulating or bending of a trunk of a patient in a supine, prone or lateral position.

Current surgical practice incorporates imaging techniques and technologies throughout the course of patient examination, diagnosis and treatment. For example, minimally invasive surgical techniques, such as percutaneous insertion of spinal implants, involve small incisions that are guided by continuous or repeated intra-operative imaging. These images can be processed using computer software programs that produce three dimensional images for reference by the surgeon during the course of the procedure. If the patient support surface is not radiolucent or compatible with the imaging technologies, it may be necessary to interrupt the surgery periodically in order to remove the patient to a separate surface for imaging followed by transfer back to the operating support surface for resumption of the surgical procedure. Such patient transfers for imaging purposes may be avoided by employing radiolucent and other imaging compatible systems. The patient support system should also be constructed to permit unobstructed movement of the imaging equipment and other surgical equipment around, over and under the patient throughout the course of the surgical procedure without contamination of the sterile field.

It is also necessary that the patient support system be constructed to provide optimum access to the surgical field by the surgery team. Some procedures require positioning of portions of the patient's body in different ways at different times during the procedure. Some procedures, for example, spinal surgery, involve access through more than one surgical site or field. Since all of these fields may not be in the same plane or anatomical location, the patient support surfaces should be adjustable and capable of providing support in different planes for different parts of the patient's body as well as different positions or alignments for a given part of the body. Preferably, the support surface should be adjustable to provide support in separate planes and in different alignments for the head and upper trunk portion of the patient's body, the lower trunk and pelvic portion of the body as well as each of the limbs independently.

Certain types of surgery, such as orthopedic surgery, may require that the patient or a part of the patient be repositioned during the procedure while in some cases maintaining the sterile field. Where surgery is directed toward motion preservation procedures, such as by installation of artificial joints, spinal ligaments and total disc prostheses, for example, the surgeon must be able to manipulate certain joints while supporting selected portions of the patient's body during surgery in order to facilitate the procedure. It is also desirable to be able to test the range of motion of the surgically repaired or stabilized joint and to observe the gliding movement of the reconstructed articulating prosthetic surfaces or the tension and flexibility of artificial ligaments and other types of dynamic stabilizers before the wound is closed. Such manipulation can be used, for example, to verify the correct positioning and function of an implanted prosthetic disc or joint replacement during a surgical procedure. Where manipulation discloses binding, sub-optimal position or even crushing of the adjacent vertebrae, for example, as may occur with osteoporosis, the prosthesis can be removed and the adjacent vertebrae fused while the patient remains anesthetized. Injury which might otherwise have resulted from a "trial" use of the implant post-operatively will be avoided, along with the need for a second round of anesthesia and surgery to remove the implant or prosthesis and perform the revision, fusion or corrective surgery.

There is also a need for a patient support surface that can be rotated, articulated and angulated so that the patient can be moved from a prone to a supine position or from a prone to a 90° position and whereby intra-operative extension and flexion of at least a portion of the spinal column can be achieved. The patient support surface must also be capable of easy, selective adjustment without necessitating removal of the patient or causing substantial interruption of the procedure.

For certain types of surgical procedures, for example spinal surgeries, it may be desirable to position the patient for sequential anterior and posterior procedures. The patient support surface should also be capable of rotation about an axis in order to provide correct positioning of the patient and optimum accessibility for the surgeon as well as imaging equipment during such sequential procedures.

Orthopedic procedures may also require the use of traction equipment such as cables, tongs, pulleys and weights. The patient support system must include structure for anchoring such equipment and it must provide adequate support to withstand unequal forces generated by traction against such equipment.

Articulated robotic arms are increasingly employed to perform surgical techniques. These units are generally designed to move short distances and to perform very precise work. Reliance on the patient support structure to perform any necessary gross movement of the patient can be beneficial, especially if the movements are synchronized or coordinated. Such units require a surgical support surface capable of smoothly performing the multi-directional movements which would otherwise be performed by trained medical personnel. There is thus a need in this application as well for integration between the robotics technology and the patient positioning technology.

While conventional operating tables generally include structure that permits tilting or rotation of a patient support surface about a longitudinal axis, previous surgical support devices have attempted to address the need for access by providing a cantilevered patient support surface on one end.

Such designs typically employ either a massive base to counterbalance the extended support member or a large overhead frame structure to provide support from above. The enlarged base members associated with such cantilever designs are problematic in that they may obstruct the movement of C-arm mobile fluoroscopic imaging devices. Surgical tables with overhead frame structures are bulky and may require the use of dedicated operating rooms, since in some cases they cannot be moved easily out of the way. Neither of these designs is easily portable or storable.

Thus, there remains a need for a patient support system that provides easy access for personnel and equipment, that can be easily and quickly positioned and repositioned in multiple planes without the use of massive counterbalancing support structure, and that does not require use of a dedicated operating room.

SUMMARY OF THE INVENTION

The present invention is directed to a patient support system that permits adjustable positioning, repositioning and selectively lockable support of a patient's head and upper body, lower body and limbs in up to a plurality of individual planes while permitting tilting, rotation, angulation or bending and other manipulations as well as full and free access to the patient by medical personnel and equipment. The system of the invention includes at least one support end or column that is height adjustable. The illustrated embodiment includes a pair of independently height-adjustable end support columns. The columns may be independent or connected to a horizontally length-adjustable base. One support column according to the invention may be coupled with a wall mount or other stationary support. A patient support structure is connected to and bridges substantially between the pair of end supports. The support structure may be a frame or other patient support having at least first and second hingable or pivotally connected portions, the first and second portions being selectively lockable in a first substantially planar orientation along a longitudinal axis of the support structure. The first and second portions are also positionable and lockable in a plurality of angles with respect to one another, with each portion being movable to a position on either side of the first planar orientation. In other words, the patient support structure is capable of hinging or otherwise bending to form an angulation or break, either upwardly or downwardly when the support structure is in a substantially horizontal position and also when the support structure is in an inclined position due to one of the support columns raising one end of the structure higher than another end. Of course, such a break may be from side-to-side when the support structure is rotated about a longitudinal axis thereof.

In a particular illustrated embodiment, angulation or breaking of the support structure is supported by a cable drive system (tension band suspension) that supports angulation using stationary end supports. Other embodiments include cantilevered systems with connected or unconnected movable or telescoping base supports. The first and second support structure portions may be in the form of frames, such as rectangular frames or other support structure that may be equipped with support pads for holding the patient, or other structure, such as imaging tops.

The patient support structure and the support column or columns are coupled with respective rotation, articulation or angulation adjustment structure for positioning the first support portion with respect to a first column or end support and with respect to the second support portion and the second support portion with respect to the second column or end support. Rotation adjustment structure in cooperation with pivoting and height adjustment structure provide for the lockable positioning of the first and second patient support portions at a variety of selected positions and articulations with respect to the support columns including angulation coupled with Trendelenburg and reverse Trendelenburg configurations as well as providing for patient roll over in horizontal or tilted orientation. Lateral movement (toward and away from a surgeon) may also be provided by a bearing block feature. A pair of patient support structures (such as a support frame and an imaging table) may be mounted between end supports of the invention and then rotated in unison about a longitudinal axis to achieve 180° repositioning of a patient, from a prone to a supine position.

Various objects and advantages of this invention will become apparent from the following description taken in relation to the accompanying drawings wherein are set forth, by way of illustration and example, certain embodiments of this invention.

The drawings constitute a part of this specification, include exemplary embodiments of the present invention, and illustrate various objects and features thereof.

BRIEF DESCRIPTION OF THE DRAWINGS

Figure 1:
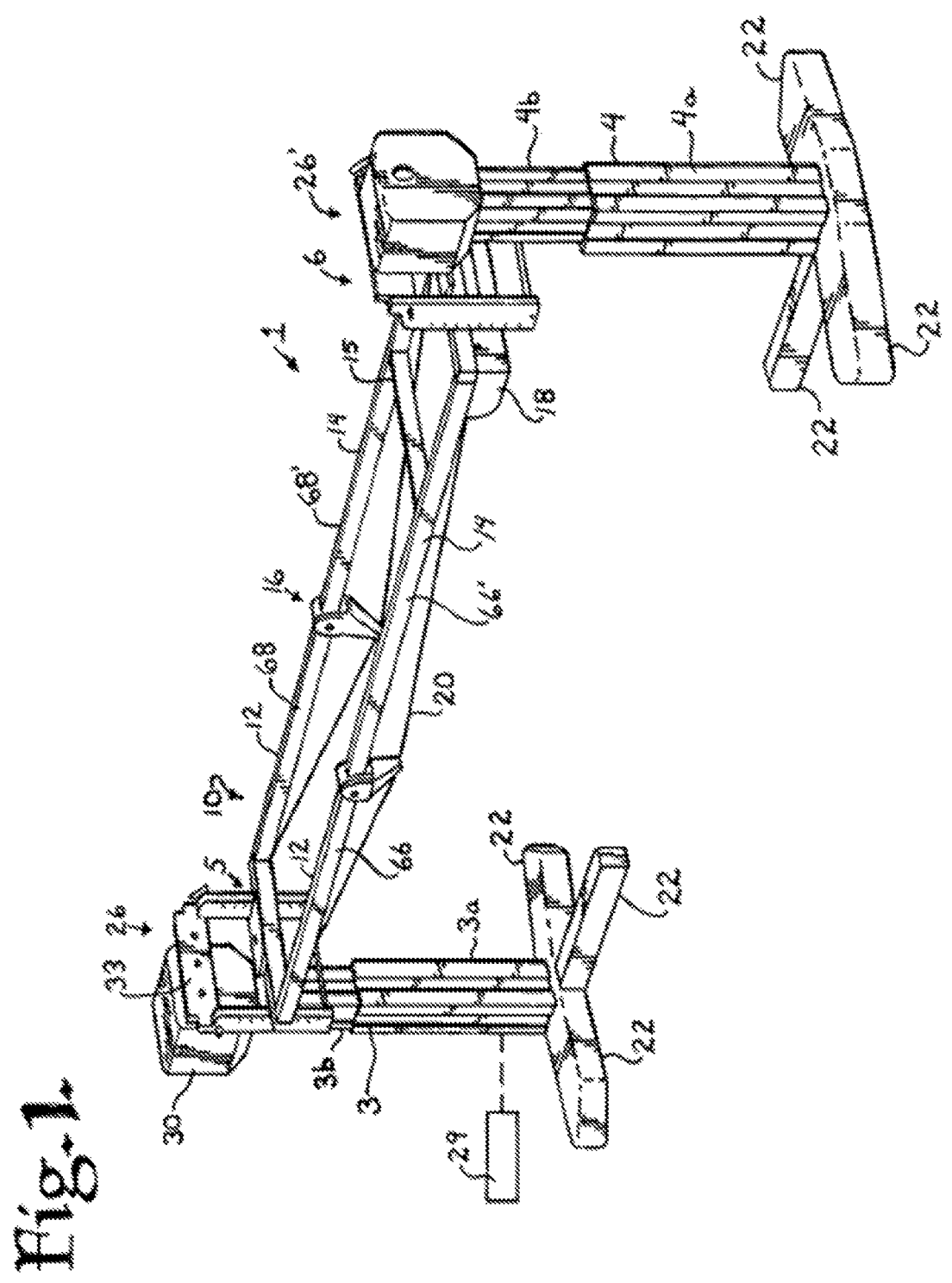

FIG. 1 is a perspective view of a patient support structure according to the invention.

FIG. 2 is an enlarged and partial side elevational view of a portion of the support structure of FIG. 2.

FIG. 3 is an enlarged and partial top plan view of the support structure of FIG. 1.

FIG. 4 is an enlarged and partial perspective view of a portion of the structure of FIG. 1.

FIG. 5 is an enlarged and partial side elevational view of a portion of the structure of FIG. 1.

FIG. 6 is an enlarged and partial perspective view of a portion of the structure of FIG. 1.

FIG. 7 is an enlarged and partial perspective view of a first hinge of the structure of FIG. 1.

FIG. 8 is an enlarged and partial perspective view of a cooperating second hinge of the structure of FIG. 1.

FIG. 9 is an enlarged and partial elevational view of the hinge of FIG. 7.

FIG. 10 is an enlarged and partial perspective view of an outer portion of the hinge of FIG. 7 with portions broken away to show the detail thereof.

FIG. 13 is a partial perspective view of a patient support frame of the structure of FIG. 1.

FIG. 14 is a partial perspective view of a patient imaging top for replacement with the patent support frame of FIG. 13.

DETAILED DESCRIPTION OF THE ILLUSTRATED EMBODIMENTS

Figure 11:
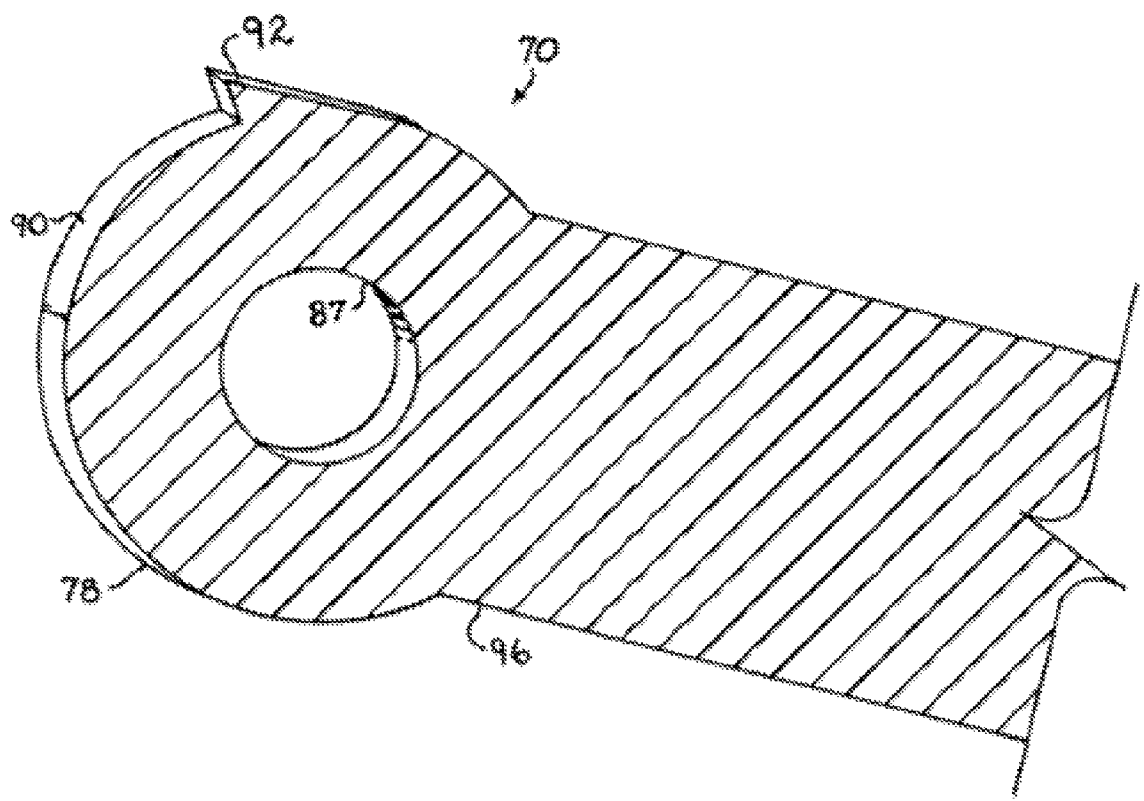
FIG. 11 is an enlarged and partial perspective view of an inner portion of the hinge of FIG. 7 with portions broken away to show the detail thereof.
Figure 12:
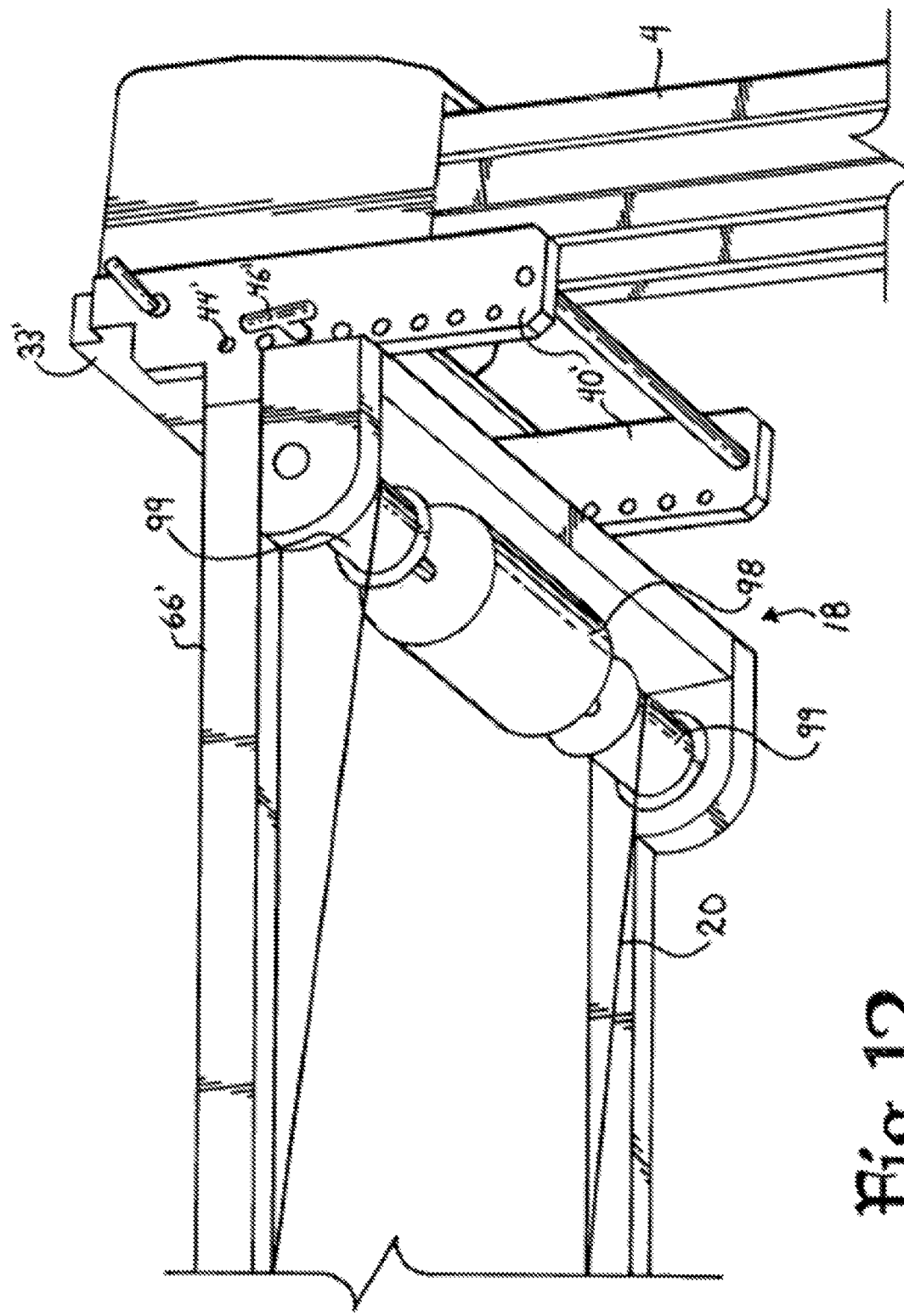
FIG. 12 is an enlarged and partial perspective view of a portion of the structure of FIG. 1 showing a cable drive motor and winch cylinders.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring now to the drawings, a patient positioning support structure according to the invention is generally designated by the reference numeral 1 and is depicted in FIGS. 1-12. The structure 1 includes first and second upright support piers or columns 3 and 4 which are illustrated as independent, stationary floor base support structures as shown in FIG. 1 or may be connected to one another by a non-telescoping base support as illustrated in the embodiment shown in FIGS. 25-28. In some embodiments according to the invention as shown, for example, in FIGS. 31-33, the base connection places the columns in a selectively telescoping relationship. It is also foreseen that in certain embodiments according to the invention, one of the support columns may be replaced by a conventional operating table support, or may even be a wall mount. In the illustrated embodiment, the upright support column 3 is connected to a first support assembly, generally 5, and the upright support column 4 is connected to a second support assembly, generally 6. Between them, the support assemblies 5 and 6 uphold an elongate and angulatable or breaking patient holding or support structure, generally 10 and optionally, a removable patient support structure that will be described with respect to another embodiment of the invention. The illustrated support structure 10 includes a first frame section 12, a second frame section 14 with a transverse support cross bar 15, and a pivot or hinge assembly, generally 16. In the illustrated embodiment, the pivot assembly further includes a cable drive system including a dual winch 18 and cooperating cables 20.

The columns 3 and 4 are supported by outwardly extending feet 22 that may or may not include spaced apart casters or wheels (not shown) each equipped with a floor-lock foot lever for lowering the feet 12 into a floor-engaging position as shown in FIG. 1. The columns 3 and 4 each include two or more telescoping lift arm segments 3a, 3b and 4a, 4b, respectively that permit the height of each of the columns 3 and 4 to be selectively increased and decreased in order to raise and lower all or a selected portion of the connected patient support structure 10. It is foreseen that the vertical supports 3 and 4 may be constructed so that the column 3 has a greater mass than the support column 4 or vice versa in order to accommodate an uneven weight distribution of the human body. Such reduction in size at the foot end of the system 1 may be employed in some embodiments to facilitate the approach of personnel and equipment.

Each of the support assemblies 5 and 6 generally includes a rotation subassembly 26 and 26' and an angulation subassembly 27 and 27', respectively, that are interconnected as will be described in greater detail below and include associated power source and circuitry linked to a controller 29 (FIG. 1) for cooperative and integrated actuation and operation. The rotational subassemblies 26 and 26' enable coordinated rotation of the patient support structure 10 about a longitudinal axis. The angulation subassemblies 27 and 27' enable the selective hinging or breaking of the support 10 by the hinge assembly 16 at desired levels and increments as well as selective tilting of the longitudinal axis of the frame portion 12 or 14. The rotation subassembly or mechanism 26 is shown in FIG. 5 and includes at least one motor housing 30 surmounting the support column 3. In the illustrated embodiment, only one rotational motor is provided, but it is foreseen that a cooperating motor may also be mounted on the support column 4. A main rotational shaft 32 extends from the motor housing 30 that turns a rotation structure 33. The rotation structure 33 in turn rotates the connected patient support 10 about a longitudinal axis as will be described in greater detail below. The motor housing 30 contains a rotary electric motor or other actuator drivingly engaged with the shaft 32. The rotation mechanism 26 is operated by actuating the motor using a switch or other similar means. The rotation structure 33 is fixed to the shaft 32 at a location spaced from the motor housing 30 and the support column 3 to provide clearance for rotation of the connected patient support structure 10.

As shown in FIG. 5, the rotation structure 33 is attached to a pair of translation posts or H-bar posts 40 disposed at either end of the rotation structure 33. The posts 40 are each attached to the structure 33 by a pin 42, bolt, or other fixing structure. A plurality of cooperating apertures 44 formed in the posts 40 provide passageway for a pivot pin 46 to extend therethrough. The pivot pin 46 is receivable in each cooperating pair of apertures 44 allowing for selective placement of a translation connector 48 that is sized and shaped to be received between the pair of posts 40 and also receive the pivot pin 46 therethrough. The pin 46 and connector 48 are thus positionable in an orientation transverse to the longitudinal extension of the support 10 at a variety of heights to be selected by the surgeon and readily changeable, even during surgery if necessary, to vary the height of the frame section 12. The multiple location or height feature is also advantageous when more than one frame or patent structure is mounted in tandem as shown, for example in FIGS. 25-28. The position of the frame or other structure may be desirably changed to provide close proximity to an imaging top with a distance between a patient support and an imaging top being expandable or reduceable depending upon the size or other attributes of a patient and surgical or other requirements. As illustrated in FIG. 5, the connector 48 has a slot 50 for receiving the pivot pin 46.

The translation connector 48 is in turn attached to a pivot connector 52. The pivot connector 52 includes first and second outwardly opening and opposed slots 54 and 56. The first slot 54 is sized and shaped for receiving the translation connector 48 and the second slot is sized and shaped for receiving an end connection 58 of the frame section 12. The pivot connector 52 further includes a through aperture or bore 60 running substantially perpendicular to the slot 54 and communicating therewith. The aperture 60 is sized and shaped to receive a pivot pin 62 therethrough, allowing for some forward and rearward lateral movement of the attached frame end connection 58 and thus the frame section 12, providing a degree of freedom and clearance needed for rotation of the patient support about a longitudinal axis of a patient. The slot 56 is sized and shaped to frictionally engage the frame end connection 58, thus securely fixing the end connection 58 to the pivot connector 52. The frame end connection 58 is in turn fixed to each of elongate frame members 66 and 68 of the frame section 12. The frame members 66 and 68 are each hingedly connected to the hinge assembly 16 to be described in greater detail below. Pivoting of the translation connector 48 with respect to the pin 46 provides for selected articulation of the frame section 12 (that includes the end connection 58 and the frame members 66 and 68) and/or the entire support 10 with respect to the support pier or column 3.

With reference to FIG. 6, at the support pier or column 4, the support assembly 6 is substantially similar to the support assembly 5 with the exception that the rotation subassembly 26' is passive and therefore does not include a motor. However, the support pier or column 4 preferably includes a powered mechanism to provide selective height adjustment of the subassembly 26'. A rotation structure 33' is spaced from and freely rotatable with respect to the column 4. The structure 33' includes a shaft (not shown) extending outwardly therefrom similar to the rotation shaft 32, the shaft being rotatingly received in an aperture in the support column 4.

The rotation subassembly 26' and the angulation subassembly 27 otherwise include elements identical to or substantially similar to the elements of the subassemblies 26 and 27. Specifically, H-bar posts 40', pin 42', apertures 44', pivot pin 46', translation connector 48', slot 50', pivot connector 52', end connector 58' and pivot pin 62', are identical or substantially similar in form and cooperate with other elements identically or substantially similarly to what has been described previously herein with respective H-bar posts 40, pin 42, apertures 44, pivot pin 46, translation connector 48, slot 50, pivot connector 52, end connector 58 and pivot pin 62.

Figure 21:
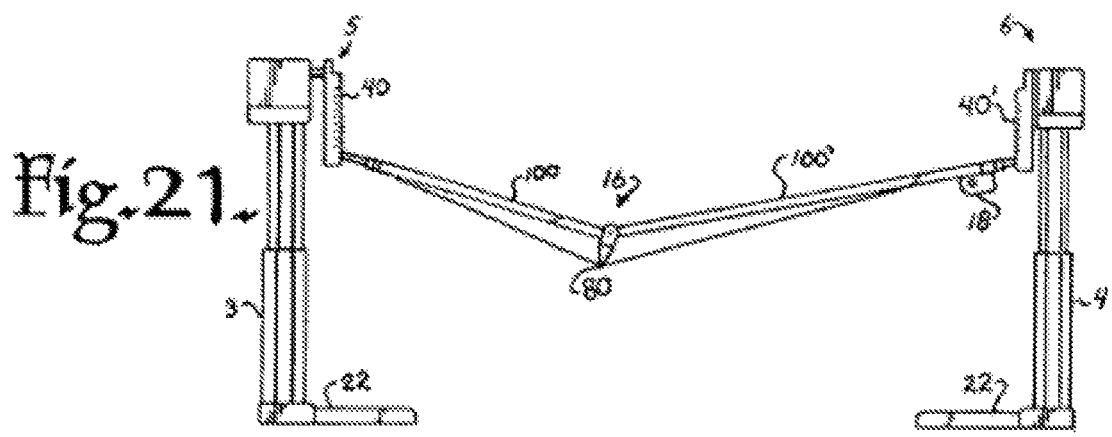
FIG. 21 is a side elevational view of the structure of FIG. 15 shown in a symmetrical downward breaking position.

The frame 14 further includes frame members 66' and 68' that are each fixed to the end connector 58'. The frame members 66' and 68' are pivotably or hingedly connected to respective frame members 66 and 68 by the hinge assembly 16. Specifically, the frame member 66 is attached to the frame member 66' by the hinge mechanism 70 and the frame member 68 is attached to the frame member 68' by the hinge mechanism 72. With particular reference to FIGS. 7 and 9-11, the hinge mechanism 70 includes an outer member 76 and an inner member 78. The outer member 76 is fixed or may be integral with the elongate frame member 66, while the inner member 78 is integral or otherwise fixed to the frame member 66'. The outer member 76 further includes an extension 80 with a groove 82 for receiving and guiding the cable 20. The extension 89 tapers in a direction from the outer member interior 84 to the groove 82. The extension 89 is configured to cause a slight upward break or bend of the support 10 when the extension 89 comes into contact with the cable 20 at the groove 82. In that way, when the cables 20 are reeled in to shorten the hypotenuse of the triangle formed by the cable, the section 12 and the section 14, the sections 12 and 14 move toward one another, resulting in the upward break as illustrated, for example, in FIG. 18. The downward break illustrated, for example, in FIG. 21 is a result of lengthening the cable 20 distance and allowing gravity to drop the hinge 70. The extension 89 is shaped to extend slightly inwardly toward a longitudinal axis A of the support 10, thereby guiding the cable 20 along a path within a periphery of the frame sections 12 and 14 when the extension 89 is in contact with the cable 20 when in a downward breaking configuration directed toward the cable with the cable 20 being received at the groove 82.

It is foreseen that where an upward breaking (only) embodiment is desired according to the invention, the sections 12 and 14 may be positioned with respect to two end columns to always include a slight upward break or bend at the hinge or pivot between the sections 12 and 14. When the telescoping base is actuated to move the columns toward one another, the sections 12 and 14 would automatically further break upwardly and toward one another. Downward breaking would not be possible in such an embodiment as the maximum distance between the two end columns would still ensure a slight upward break or hinge between the sections 12 and 14. Such an embodiment would be acceptable for use because patient holding pads could be positioned on the frames 12 and 14 such that the patient would be in a substantially horizontal position even when there is a slight upward bend or break at the hinge between the sections 12 and 14. Returning to the hinge 70 of illustrated embodiment, the inner member 78 is slidingly and rotatably receivable in an interior 84 of the outer member 76. The outer member has a pair of pivot apertures 86 and the inner member has a pivot aperture 87, the apertures cooperating to create a through bore for receiving a pivot pin 88 through both the inner and outer hinge members. The interior 84 includes a curved partially cylindrical surface 89 for slidingly receiving a cooperating outer rounded and partially cylindrical surface 90 of the inner member 78. The inner member 78 further includes a downward breaking stop or projection 92 that limits a downward pivot (in a direction toward the cables 20) of the hinge 70 in the event the cables 20 should fail. The stop 92 abuts against a surface 93 of the interior 84. In the illustrated embodiment, the stop 92 limits the extent of rotation or hinging of the section 66 with respect to the section 66' to about twenty-five degrees. Upward pivot (in a direction away from the cables 20) is limited by abutment of an inner planar surface 95 with a planar surface 96 of the hinge inner member 78.

With particular reference to FIG. 8, the hinge mechanism 72 is substantially a mirror image of the hinge mechanism 70 and therefore includes the following elements: a hinge outer member 76', and inner member 78', and extension 80' with a groove 82', and interior 84' pivot apertures 86' and 88', a pivot pin 88', a curved surface 89', and outer surface 90', a stop 92', an abutment surface 93', an inner planar surface 95' and a planar surface 96'. These elements are substantially similar in shape and function to the respective hinge outer member 76, inner member 78, extension 80, groove 82, interior 84, pivot apertures 86 and 88, pivot pin 88, curved surface 89, outer surface 90, stop 92, abutment surface 93, inner planar surface 95 and planar surface 96 described herein with respect to the hinge 70.

It is noted that other hinge or pivot mechanisms may be utilized in lieu of the hinge assembly 16. For example, the polyaxial joint 95 illustrated and described in Applicant's pending U.S. patent application Ser. No. 11/062,775 filed Feb. 22, 2005, and pending U.S. patent application Ser. No. 11/159,494 filed Jun. 23, 2005, may be incorporated into the patient support structure 10 at the break between the sections 12 and 14. Both of these U.S. applications (Ser. Nos. 11/062,775 and 11/159,494) are hereby incorporated by reference herein.

The cable drive system 18 includes a rotary motor 98 cooperating with and driving by rotation a pair of winch cylinders 99 disposed on either side of the motor 98. The motor 98 and cylinders 99 are mounted to the end connector 58' located near the support column 4. Each cable 20 is attached to one of the winch cylinders 99 at one end thereof and to the end connector 58 at the other end thereof. In a first longitudinal position wherein the section 12 is substantially planar with the section 14, the cables 20 are wound about the winch cylinders 99 an amount to provide enough tension in the cables 20 to maintain such a substantially planar orientation and configuration, with the hinge extensions 82 and 82' being in contact with each of the cables 20. The motor 98 is preferably low speed and high torque for safely winding both of the cables 20 simultaneously about the cylinders 99 to draw the section 12 toward the section 14 to result in an upward breaking configuration with the hinges 70 and 72 disposed in spaced relation with the cables 20 and the hinges 70 and 72. The motor 98 may be reversed, reversing the direction of rotation of the winch cylinders 99 for slowly unwinding the cables 20 to a downward breaking configuration. As the cables 20 unwind, gravity draws the support sections 12 and 14 downward with the cables 20 being received in the grooves 82 and 82' of the hinge extensions 80 and 80'. As the cables 20 slacken, the hinges 70 and 72 continue to lower pressing down upon the cables 20.

It is noted that the frame sections 12 and 14 are typically equipped with pads (not shown) or other patient holding structure. Furthermore, with respect to FIGS. 13 and 14, the frame member sections 66 and 68 of section 12 and the frame member sections 66' and 68' of the section 14 may be replaced with substantially rectangular imaging tops or sections 100 and 101' respectively. Each of the sections 100 and 101' having elongate slots 101 formed therein to allow for attachment of the hinge mechanisms 70 and 72 in a manner identical or substantially similar to what has been described herein with respect to the frame sections 12 and 14.

Figure 15:
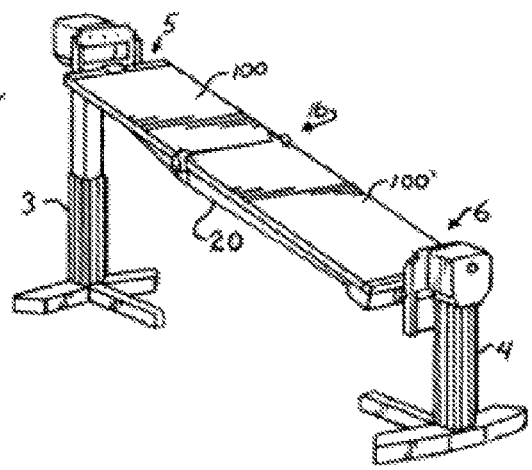
FIG. 15 is a reduced perspective view of the structure of FIG. 1 shown with an imaging top of FIG. 14 replacing the support frame of FIG. 13 and shown in a planar inclined position.
Figure 16:
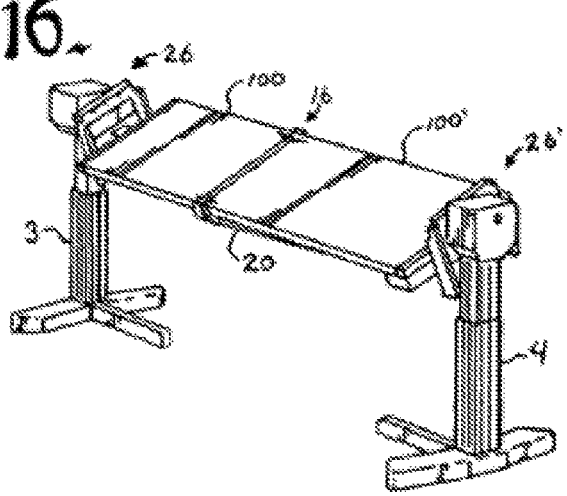
FIG. 16 is a perspective view of the structure of FIG. 15 shown in a planar tilted position.
Figure 17:
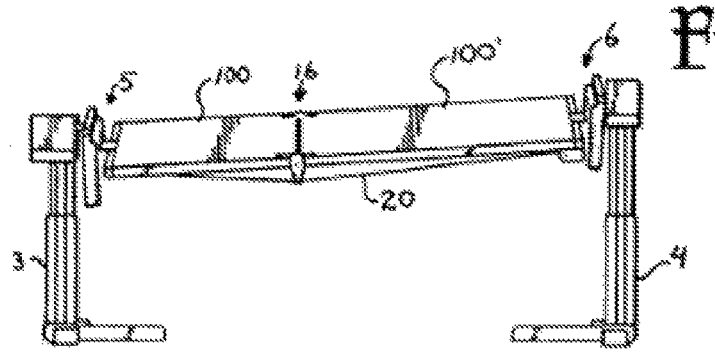
FIG. 17 is a perspective view of the structure of FIG. 15 shown in a planar inclined and tilted position.

With reference to FIGS. 15-17, the imaging sections 100 and 100' are illustrated, replacing the frame sections 12 and 14 of the embodiment disclosed in FIGS. 1-12. Each of FIGS. 15-17 represent configurations in which the cable drive 18 is tensioned such that the sections 100 and 100' are kept in a substantially coplanar configuration. FIG. 15 illustrates a configuration in which the column 3 is telescoped upwardly with the frame sections hinging at the support assemblies 5 and 6, resulting in an inclined position or configuration of the entire patient support. In the illustrated embodiment, the section 100 would preferably receive a patient's head. Therefore, FIG. 15 illustrates a reverse Trendelenburg position or orientation. FIG. 16 illustrates the sections 100 and 100' again in a substantially common plane with both sections being rotated to a tilted position produced by a powered rotation of the rotation the sub assemblies 26 and passive rotation of the assembly 26' with both columns 3 and 4 otherwise holding the sections 100 and 100' at the same height. FIG. 17 illustrates both tilting due to rotation of the assemblies 26 and 26' and also a sloping or inclined position with the column 4 being extended vertically. Thus, FIG. 17 illustrates a Trendelenburg position or orientation with both the sections 100 and 100' remaining in substantially the same plane.

Figure 18:
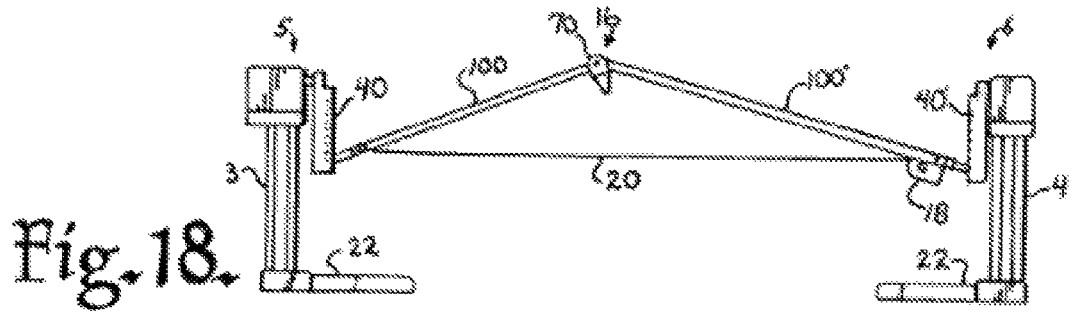
FIG. 18 is a side elevational view of the structure of FIG. 15 shown in a symmetrical upward breaking position.
Figure 19:
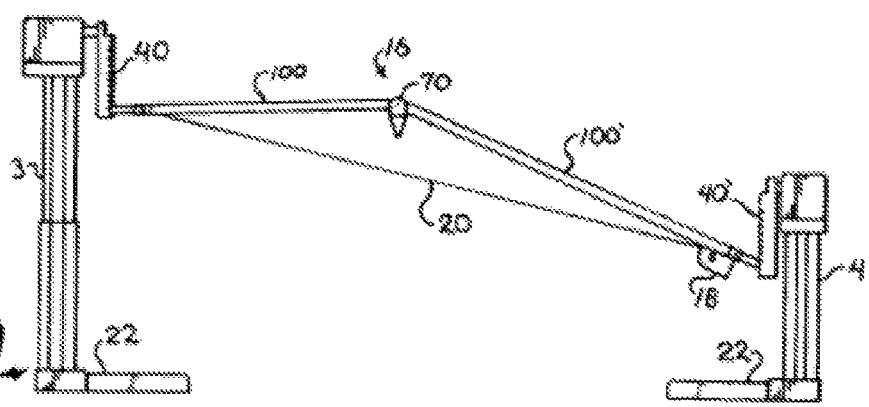
FIG. 19 is a side elevational view of the structure of FIG. 15 shown in a first inclined and upward breaking position.
Figure 20:
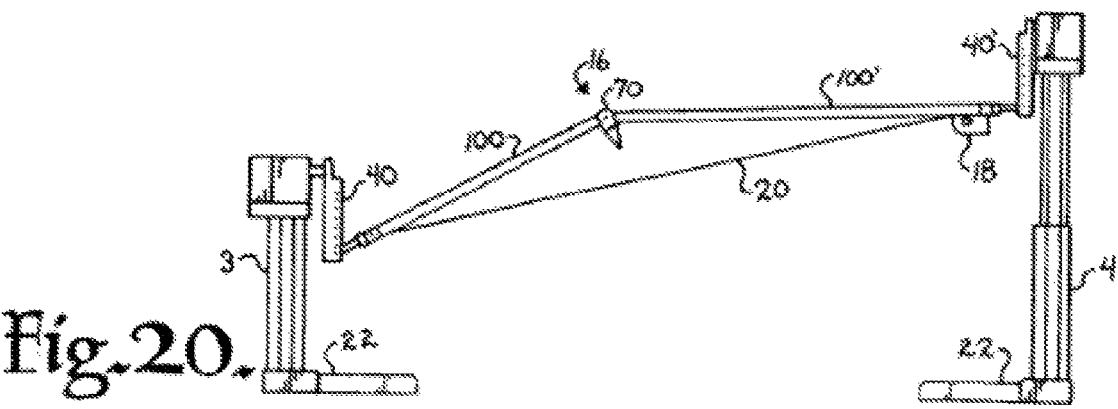
FIG. 20 is a side elevational view of the structure of FIG. 15 shown in a second inclined and upward breaking position.

With reference to FIGS. 18-20, there is illustrated three upward breaking or hinging configurations of the structure 1. FIG. 18 illustrates a symmetrical upward breaking configuration wherein the columns 3 and 4 are holding the respective support assemblies 5 and 6 at substantially the same height with the cables 20 being shortened by rotation of the winch motor to result in an upward break in the hinge assembly 16. FIG. 19 illustrates the column 3 being extended to a maximum height and the cables reeled to shorten a distance between the sections 100 and 100'. An example of such an upward break with reverse Trendelenburg would be a head or column 3 height of 43 inches, a foot or column 4 height of 24 inches and a 35 degree upward break with zero degree roll. FIG. 20 illustrates an upward breaking Trendelenburg with the column 4 being extended to a maximum height.

Figure 22:
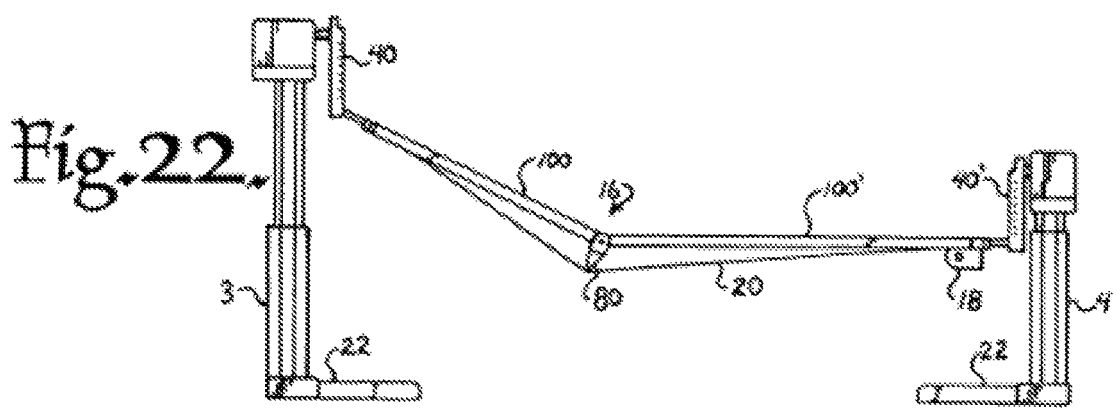
FIG. 22 is a side elevational view of the structure of FIG. 15 shown in a first inclined and downward breaking position.
Figure 23:
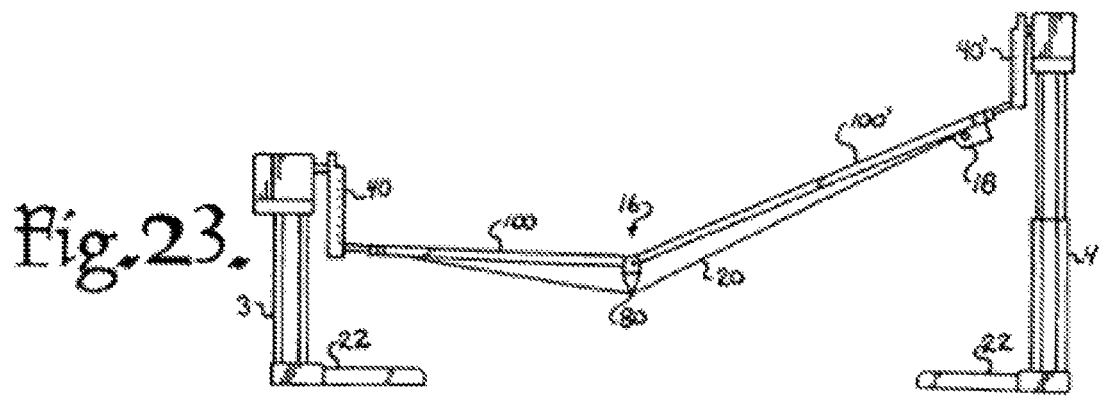
FIG. 23 is a side elevational view of the structure of FIG. 15 shown in a second inclined and downward breaking position.

With reference to FIGS. 21-23, there is illustrated three downward breaking configurations of the structure 1. FIG. 21 illustrates a symmetrical downward breaking configuration wherein the columns 3 and 4 are holding the support assemblies 5 and 6 respectively, at the same height with the cables 20 being unwound or slackened to result in a downward break in the hinge assembly 16, the hinges 70 and 72 contacting the cables 20. FIG. 22 illustrates a downward breaking reverse Trendelenburg with the column 3 being extended to a maximum height resulting in a patent's head end being at a maximum height. FIG. 23 illustrates a downward breaking Trendelenburg with the column 4 being extended to a maximum height.

Figure 24:
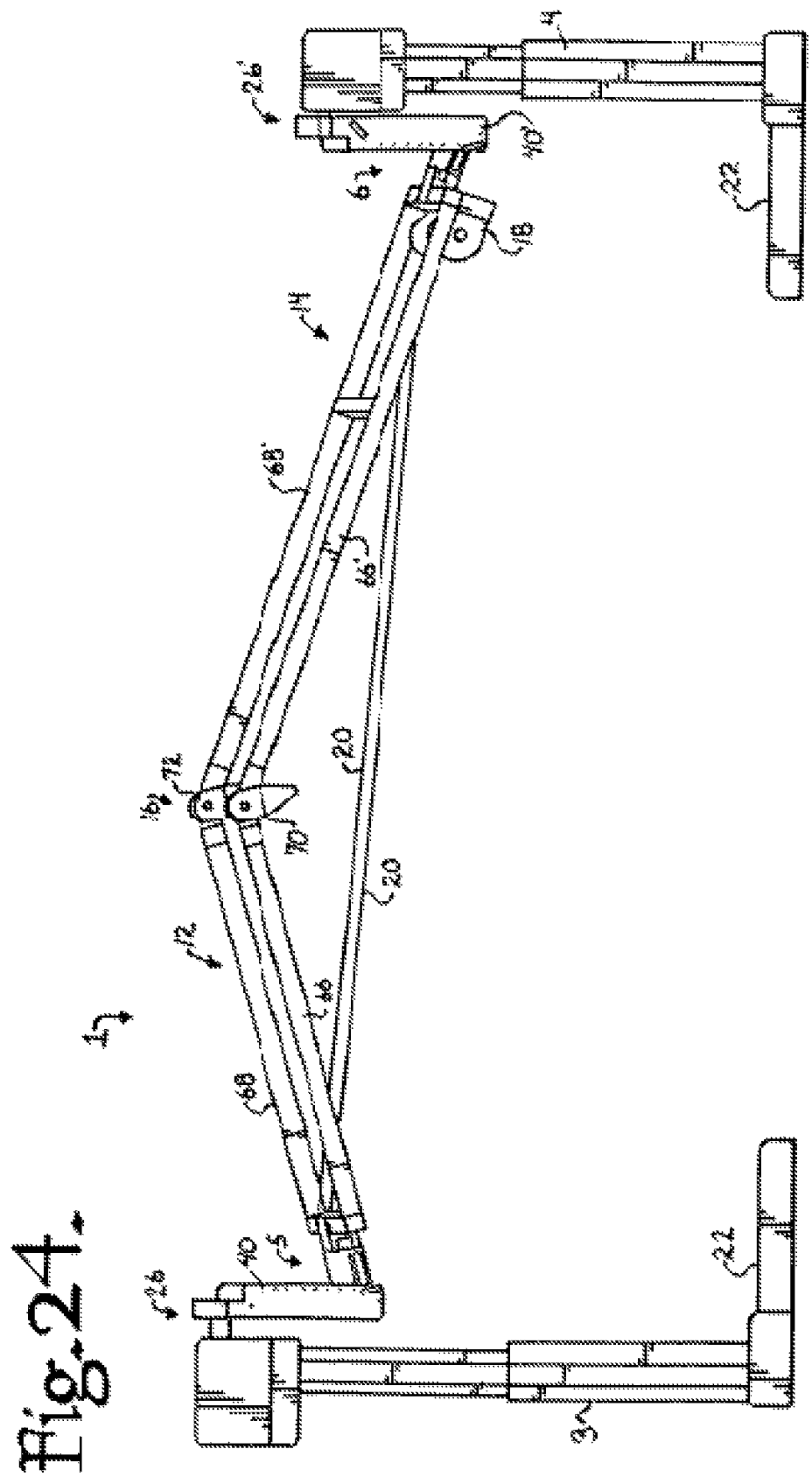
FIG. 24 is an enlarged side elevational view of the structure of FIG. 1 shown in an upward breaking, inclined and tilted position.
Figure 25:
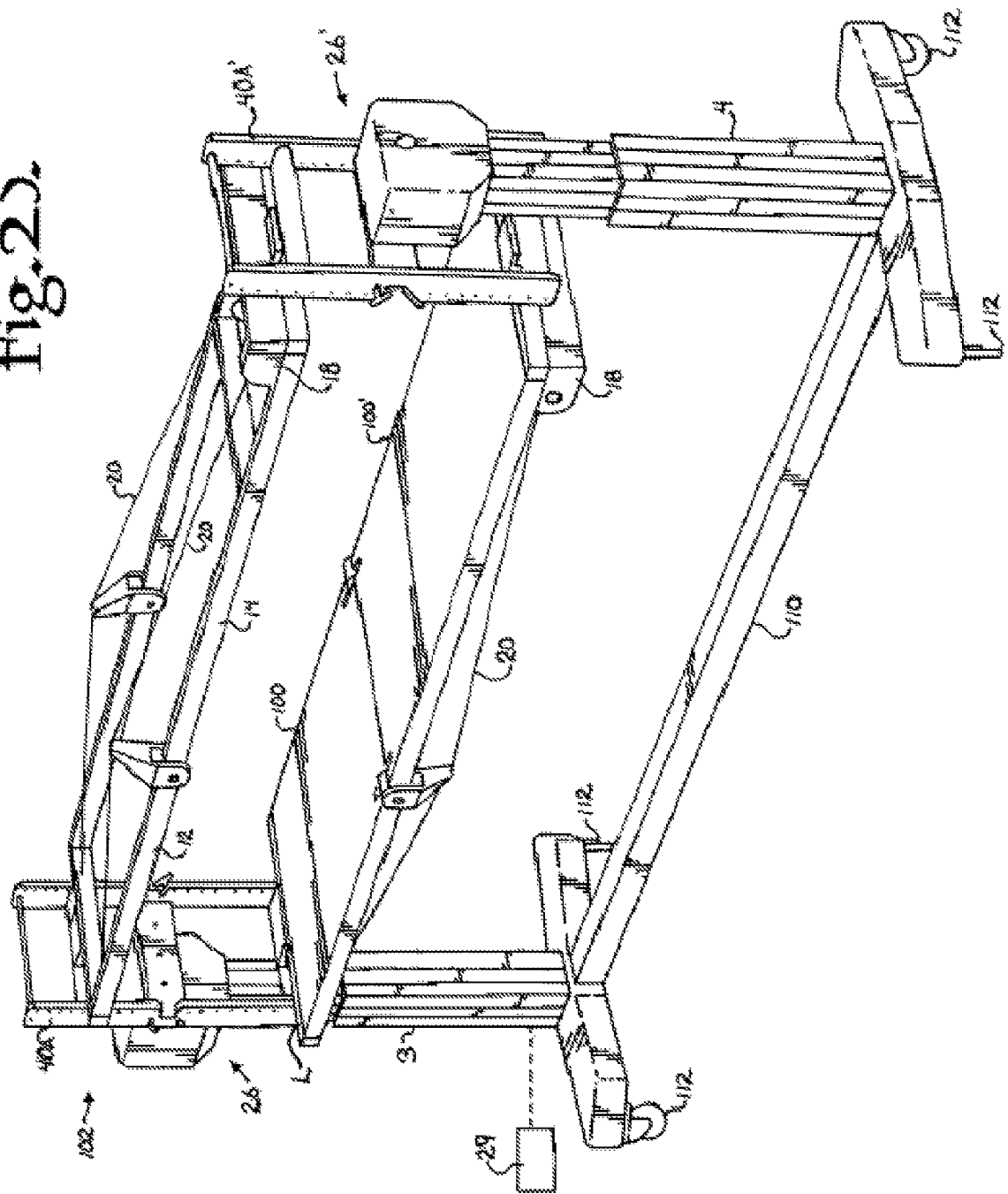
FIG. 25 is a is a perspective view of a second embodiment of a patient support structure according to the invention.
Figure 26:
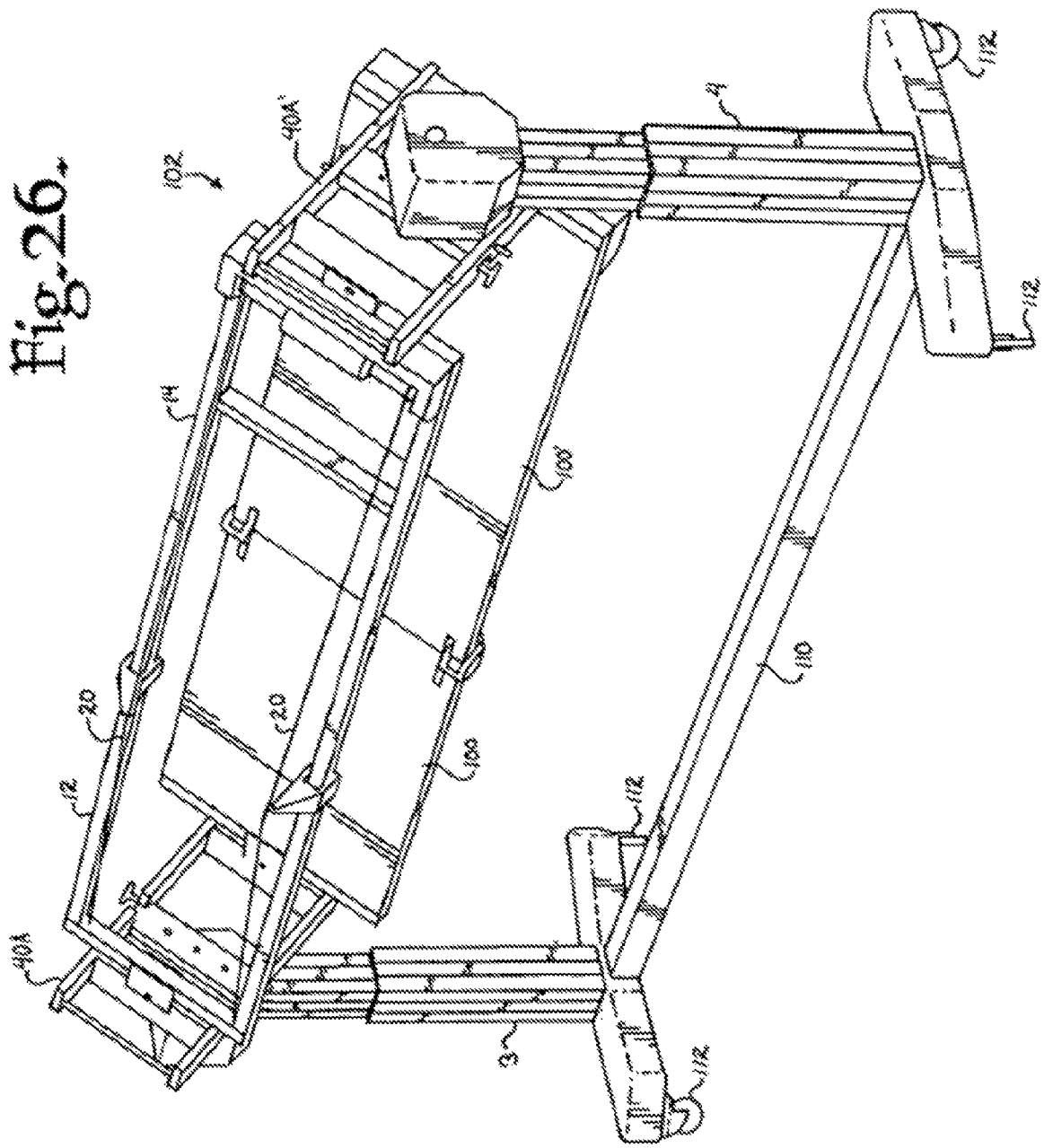
FIG. 26 is a perspective view of the patient support structure of FIG. 25 shown tilted in an intermediate position during a rotation as would be used for a patient rollover.
Figure 27:
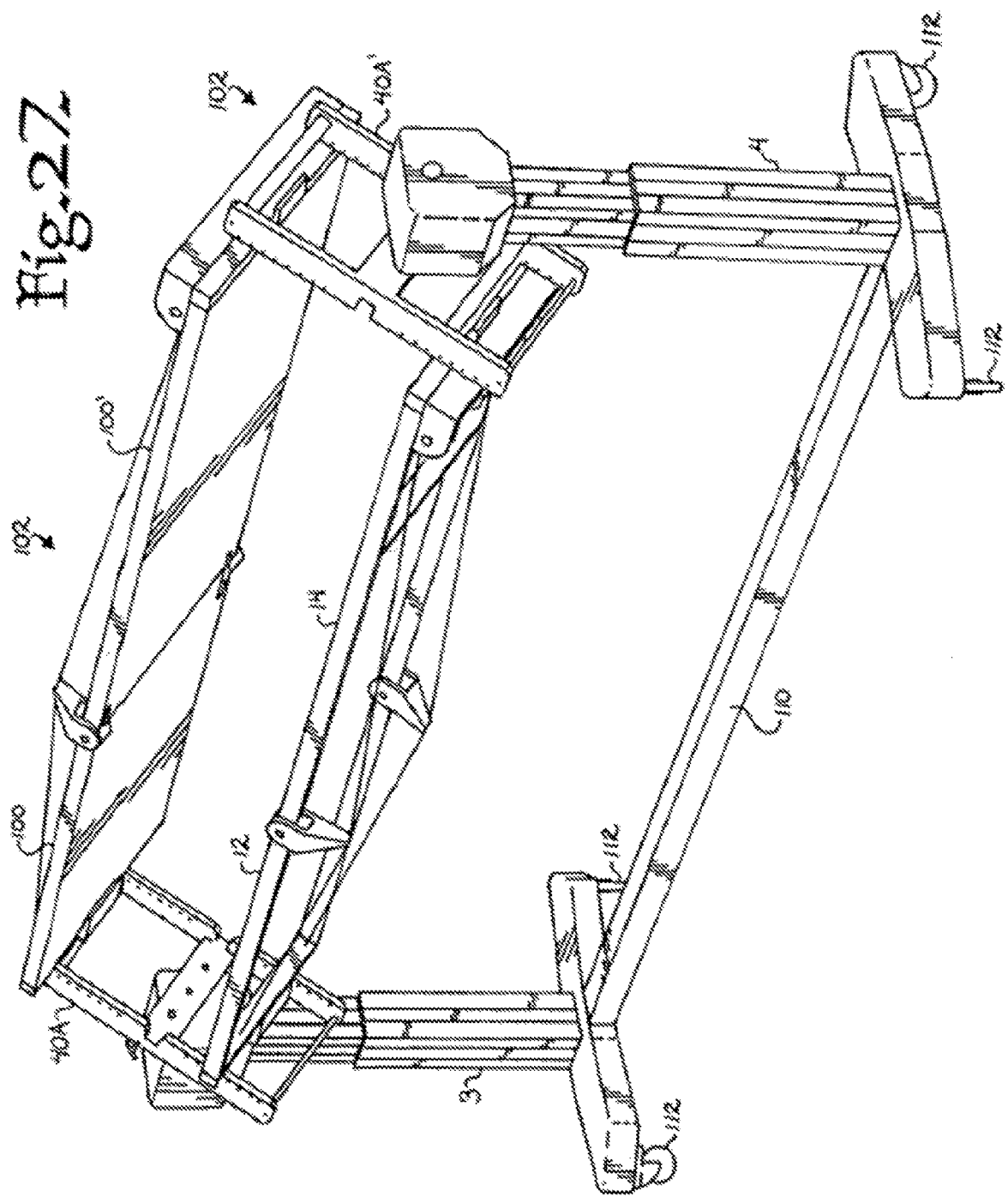
FIG. 27 is a perspective view of the structure of FIG. 25 shown further tilted in a second intermediate position during rotation.
Figure 28:
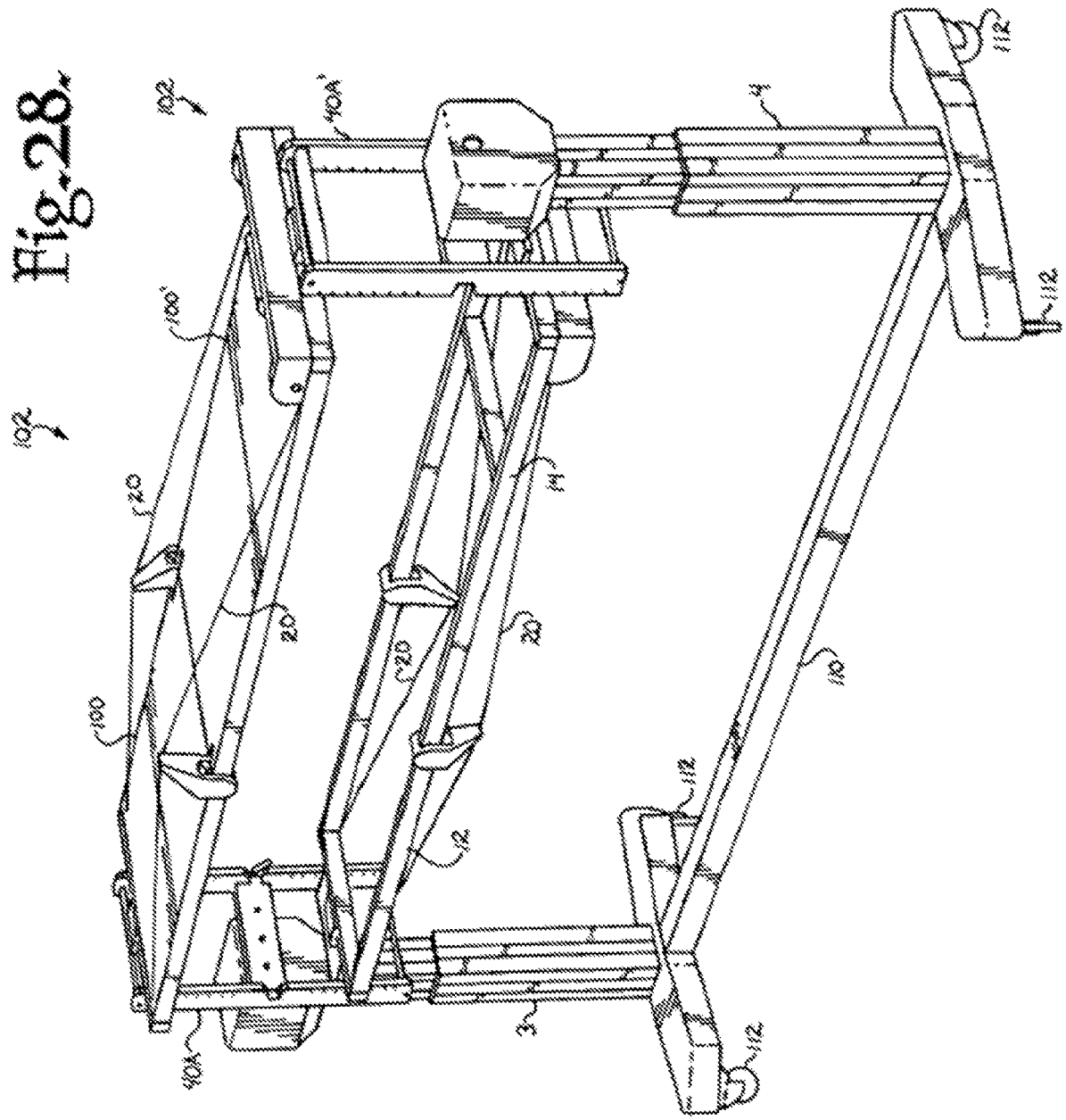
FIG. 28 is a perspective view of the structure of FIG. 25 shown after rotation to a final flipped position.

It is noted that in each of the configurations illustrated in FIGS. 18-23, the sub assemblies 26 may be rotated in either direction, resulting in a tilted or rotated as well as upwardly or downwardly broken or hinged configuration. For example, FIG. 24 illustrates the structure 1 with support frame sections 12 and 14 positioned in a configuration similar to that illustrated in FIG. 19, but also including rotation, resulting in a tilting and upwardly breaking configuration of the structure 1. An example of the position illustrated in FIG. 24 would be: a head or column 3 height of 41 inches, a foot or column 4 height of 34 inches and a 35 degree upward break with 10 degree roll.

With reference to FIGS. 25-28, another structure, generally 102 according to the invention is illustrated. The structure 102 utilizes all of the elements described herein with respect to the structure 1 and therefore the same references numerals are used for the same elements or features. The structure 102 differs from the structure 1 in that the H-bar posts 40 and 40' are replaced or modified to be extended H-bar posts 40A and 40A', allowing for the mounting of two elongate structure 10 and cooperating cable drives 18. In the embodiment shown in FIG. 25, one of the structures 10 includes the frame member 12 and 14 while the other structure is an imaging top having sections 100 and 100'. As previously described herein, the cooperating H-bar posts 40A and 40A' equipped with a plurality of apertures allows for the placement of the support structures 10 at a variety of locations. As illustrated in FIGS. 25-28, the structure 102 provides for the complete rotation and thus a roll-over of a patient by actuation of the motor of the rotation subassembly 26 using the controller 29. The structure 102 is further illustrated with a non-telescoping base support 110 fixed to each of the columns 3 and 4 and rollers or castors 112 at the base of the structure 102.

Figure 29:
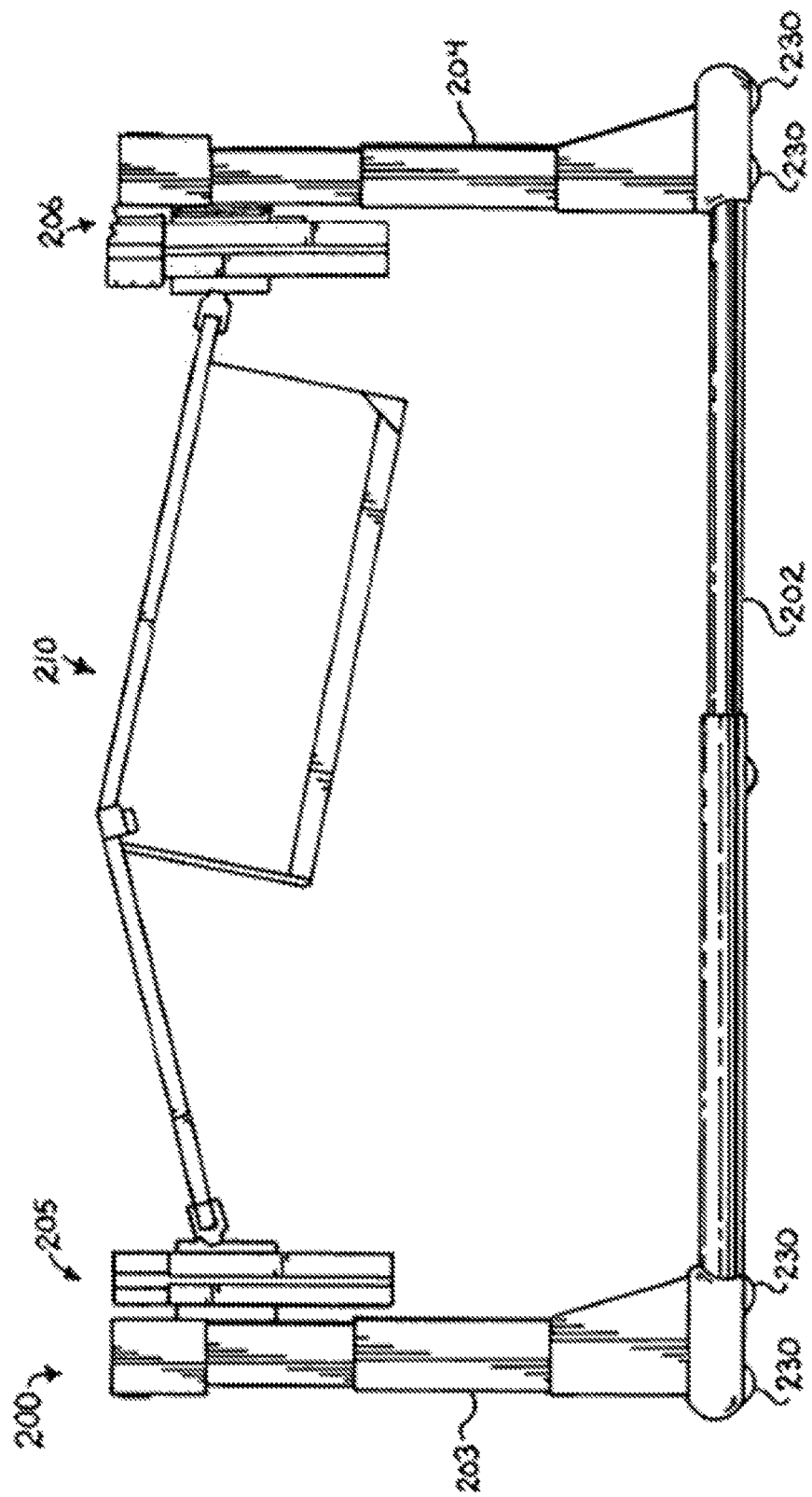
FIG. 29 is a front elevational view of a third embodiment of a patient support structure according to the invention.
Figure 30:
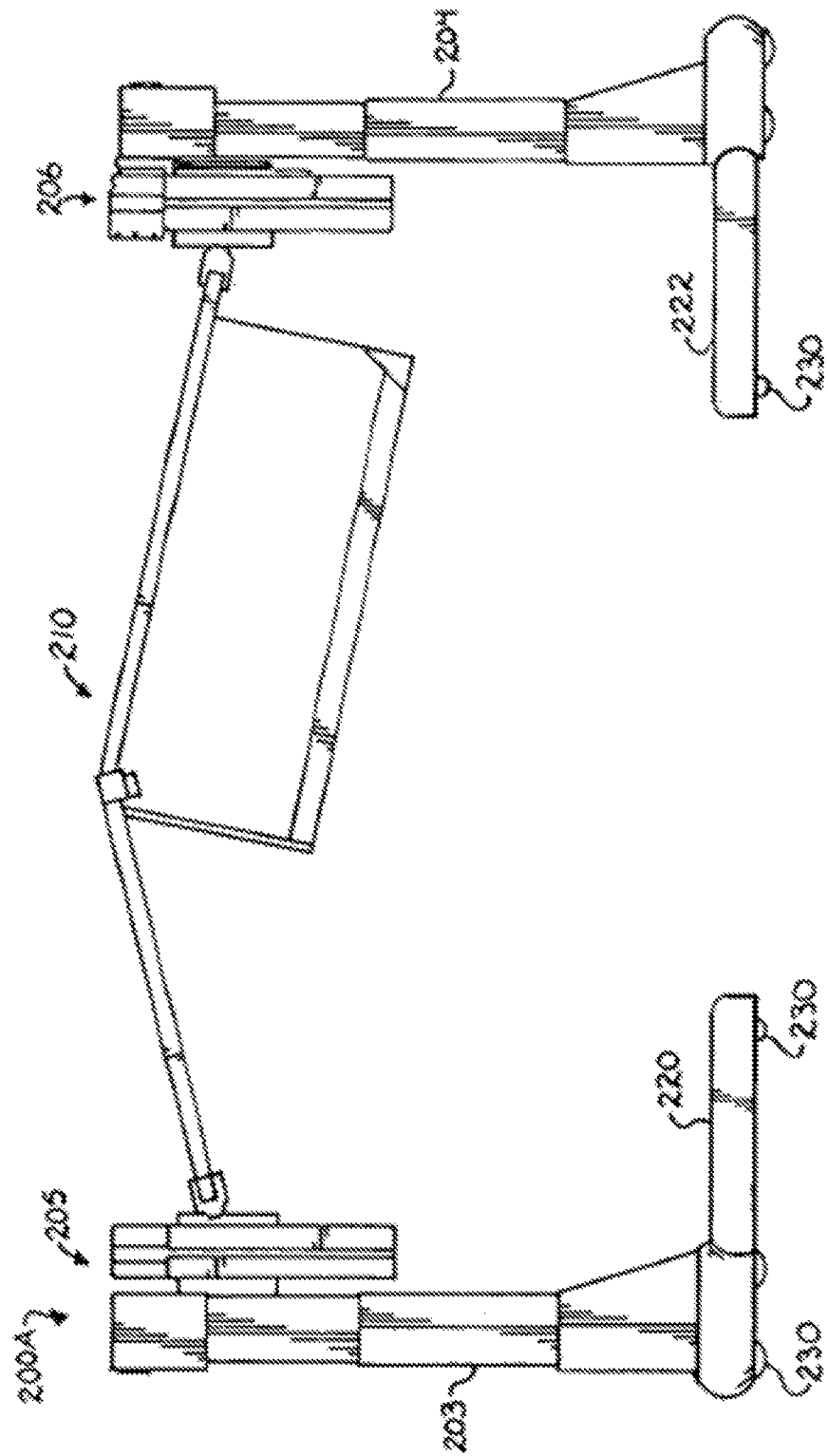
FIG. 30 is a front elevational view of a fourth embodiment of a patient support structure according to the invention.

With reference to FIGS. 29 and 30, another embodiment or system according to the invention, generally 200 is illustrated. The system 200 broadly includes an elongate length-adjustable base 202 surmounted at either end by respective first and second upright support piers or columns 203 and 204 which are connected to respective first and second support assemblies, generally 205 and 206. Between them, the support assemblies 205 and 206 uphold an elongated breaking, hingable or pivotable patient support structure, generally 210. The structure is described in detail in Applicants's pending U.S. patent application Ser. No. 11/062,775 filed Feb. 22, 2005, Ser. No. 11/159,494 filed Jun. 23, 2005, both of which are incorporated by reference herein. The embodiment 200A illustrated in FIG. 30 differs from the structure 200 only in that the length-adjustable base 202 is replaced by a first base 220 attached to the pier 203 and a second base 222 attached to the pier 204. All of the bases 202, 220 and 222 include castors or rollers 230 or some other movable structure to allow the piers 203 and 204 to move toward and away from one another during upward or downward breaking of the structure 210.

It is foreseen that cable drives as described herein, other types of motor drives including screw drives, hydraulic systems, and the like, may be utilized to facilitate both upward and downward breaking of the support structure 210.

Figure 32:
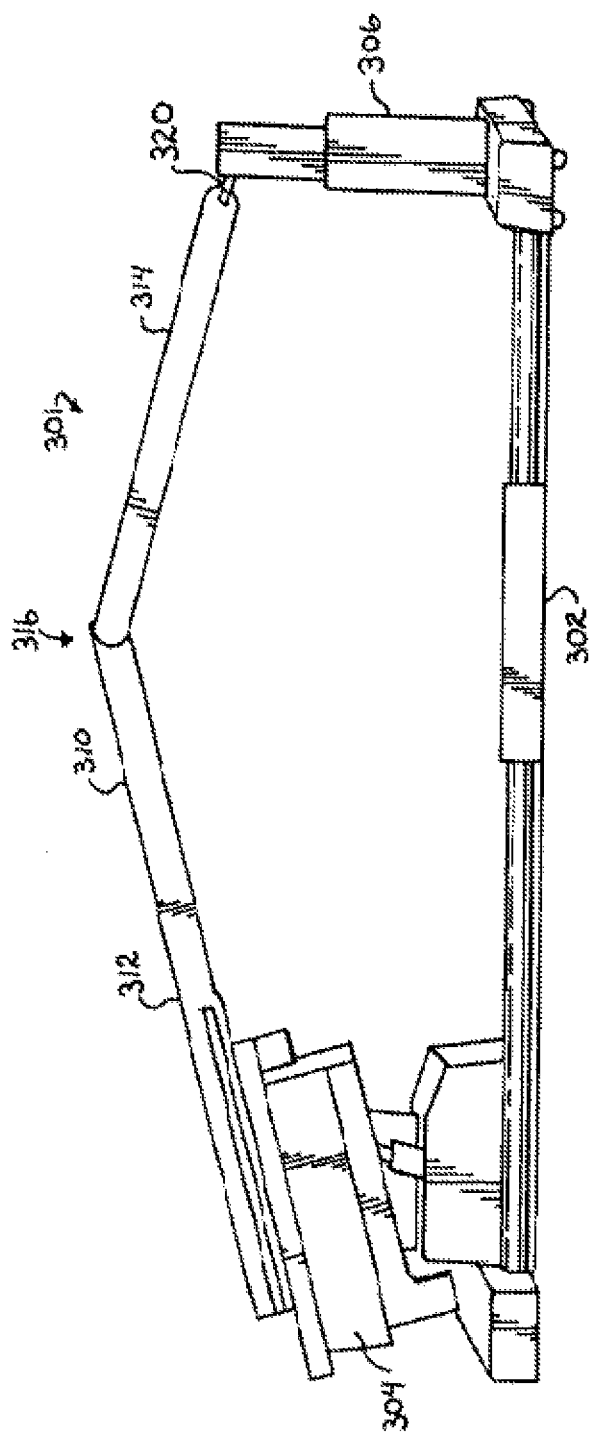
FIG. 32 is a perspective view of the structure of FIG. 31 shown in an inclined and upward breaking position.
Figure 31:
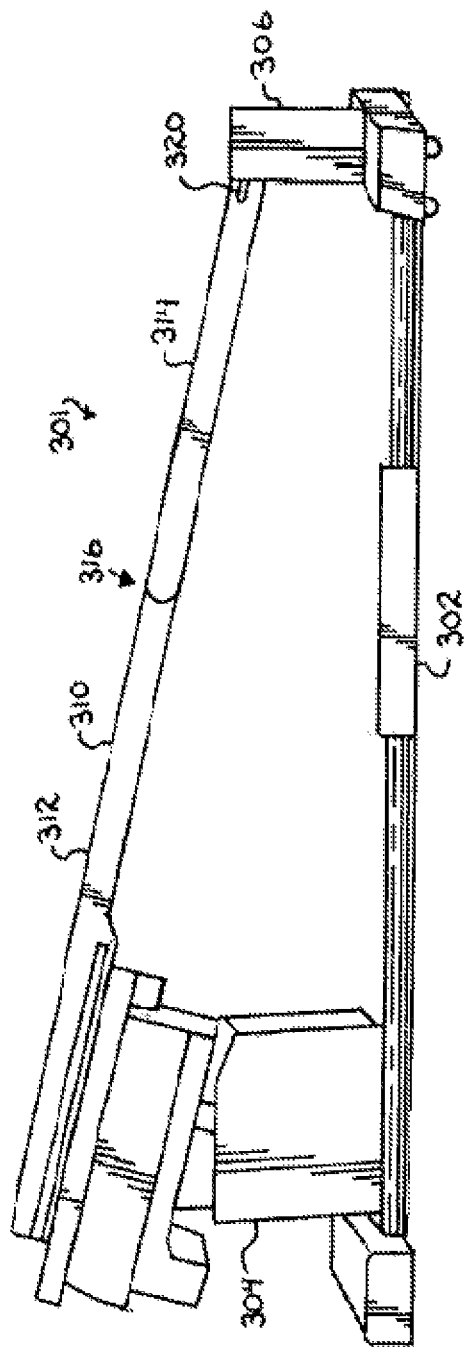
FIG. 31 is a perspective view of a fifth embodiment of a patient support structure according to the invention shown in a planar inclined position.
Figure 33:
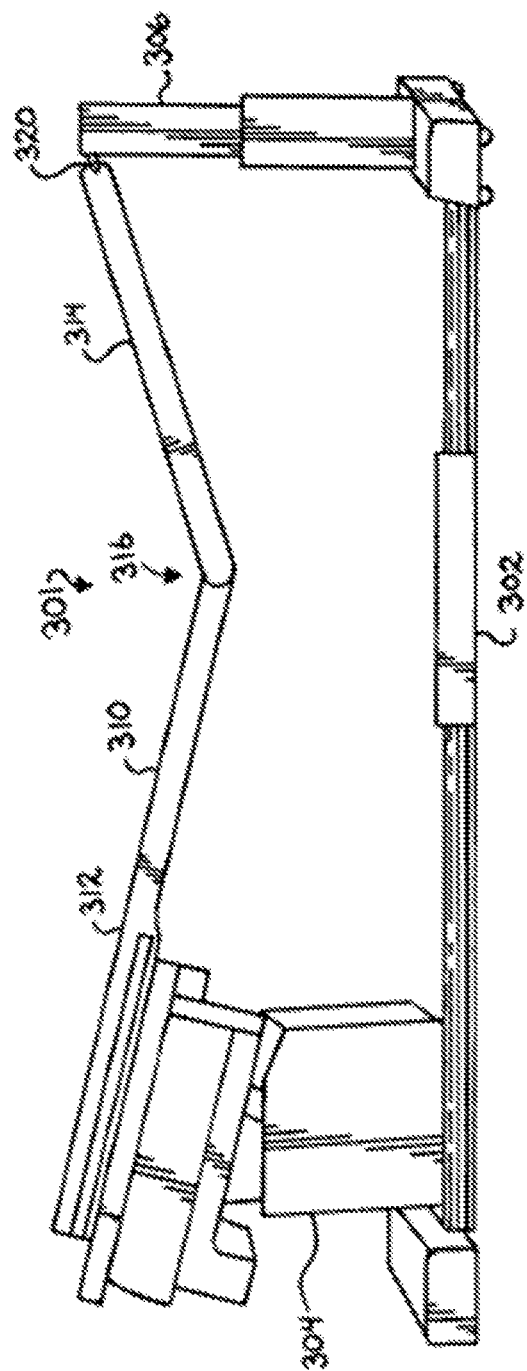
FIG. 33 is a perspective view of the structure of FIG. 31 shown in a substantially symmetrical downward breaking position.

Another patient support structure according to the invention, generally 301, is illustrated in FIGS. 31-33. The structure 301 generally includes a horizontally telescoping floor mounted base 302, a conventional or standard telescoping and inclinable operating table support structure 304, a telescoping end support or pier 306 and a hinged or pivotally upwardly and downwardly breaking support structure 310 connected to both the structure 304 and the pier 306. The patient support structure 310 further includes a first cantilevered section 312 and a second section 314. The first section 312 is fixed to and extends from the operating table support 304. The second section is attached to the pier 306 by a hinge or pivoting assembly 320, such as the support assembly 5 described herein with respect to the structure 1. The hinge mechanism 316 disposed between the support sections 312 and 314 may be a conventional hinge, pivot, or pivot or hinge systems previously described herein.

In use, the operating table support 304 utilizes electric or other power means to move the support section 312 up and down and at an incline, as is known in the art. In response to the movement of the section 312, the section 314 also moves, resulting in upward and downward breaking illustrated in FIGS. 32 and 33. In response to the movement of the section 312, the electric powered telescoping base 302 moves the pier 306 toward or away from the support 304. The pier 306 includes a motor for raising and lowering the pier at the connection 320.

As stated above with respect to other embodiments of the invention described herein, it is foreseen that cable drives as described herein, other types of drives including screw drives, hydraulic systems, and the like, may be utilized to facilitate both upward and downward breaking of the support structure 310.

It is to be understood that while certain forms of the present invention have been illustrated and described herein, it is not to be limited to the specific forms or arrangement of parts described and shown.

What is claimed and desired to be secured by Letters Patent is as follows:

1. A surgical table comprising:
   A) a patient support comprising a first segment and a second segment, the first segment comprising a first end and a second end opposite the first end, the second segment comprising a third end and a fourth end opposite the third end, the first and fourth ends forming opposite ends of the patient support, the second and third ends coupled to together to define a joint about which the first segment and second segment articulate relative to each other; and
   B) a first support structure comprising a first vertical column and supporting a first displacement apparatus operably coupling the first vertical column to the first end of the first segment of the patient support, the first displacement apparatus comprising:
      a) a first rotation assembly operably coupled to the first vertical column, the first rotation assembly configured to rotate the patient support relative to the first vertical column and about an axis parallel to a longitudinal axis of the patient support;
      b) a first angulation assembly configured to facilitate the first segment articulating relative to the second segment about the joint, the first angulation assembly comprising:
         i) a first member comprising a longitudinal length extending generally parallel to a longitudinal length of the first segment of the patient support, the first member operably coupled to the first segment near the first end, wherein displacement along the longitudinal length results in a distance between the first end of the first segment of the patient support and the first vertical column changing as the first segment and second segment articulate relative to each other about the joint; and
         ii) a first pivot located between the first end of the first segment of the patient support and the first vertical column; and
      c) a first structure operably coupling the first rotation assembly to the first member, the first structure extending downward from the first rotation assembly to the first member when the patient support faces generally upward, wherein the first member is operably coupled to the first structure via the first pivot, the first end of the first segment pivoting relative to the first vertical column about the first pivot when the first segment articulates relative to the second segment about the joint.

2. The surgical table of claim 1, further comprising a second support structure comprising a second vertical column and supporting a second displacement apparatus operably coupling the second vertical column to the fourth end of the second segment of the patient support, wherein the second vertical column is configured to vertically extend and retract, the second displacement apparatus comprising:
   a) a second rotation assembly operably coupled between the second vertical column and the fourth end of the second segment of the patient support, the rotation assembly configured to rotate the patient support relative to the second vertical column and about the axis parallel to the longitudinal axis of the patient support; and
   b) a second angulation assembly operably coupled between the second vertical column and the fourth end of the second segment of the patient support, the second angulation assembly configured to facilitate the second segment articulating relative to the first segment about the joint, the second angulation assembly comprising a second pivot between the second vertical column and the fourth end of the second segment of the patient support.

3. The surgical table of claim 2, wherein the second rotation assembly is located between the second angulation assembly and the second vertical column.

4. The surgical table of claim 3, wherein the second rotation assembly is located between the second pivot and the second vertical column.

5. The surgical table of claim 4, wherein the second pivot includes a pivot axis that is transverse to the longitudinal axis of the patient support.

6. The surgical table of claim 2, wherein the first rotation assembly comprises a first rotation shaft and the second rotation assembly comprises a second rotation shaft, wherein the first rotation shaft and the second rotation shaft each comprises a rotation axis that is parallel to a longitudinal axis of the patient support.

7. The surgical table of claim 6, wherein, when the patient support faces generally upward, the first pivot is located below the first rotation shaft, and the second pivot is located below the second rotation shaft.

8. The surgical table of claim 7, wherein the first pivot is suspended off the first rotation shaft, and the second pivot is suspended off the second rotation shaft.

9. The surgical table of claim 2, wherein at least one of the first vertical column or second vertical column comprises a telescopic assembly that facilitates the vertical extension and retraction of the at least one of the first vertical column or second vertical column.

10. The surgical table of claim 2, wherein the surgical table is configured such that the patient support at least tilts laterally when the patient support rotates relative to the first vertical column and second vertical column about the axis parallel to the longitudinal axis of the patient support.

11. The surgical table of claim 2, wherein the surgical table is configured such the patient support completely rotates laterally for patient roll-over when the patient support rotates relative to the first vertical column and second vertical column about the axis parallel to the longitudinal axis of the patient support.

12. The surgical table of claim 1, wherein the joint is the only articulation location in the patient support between the first and fourth ends.

13. The surgical table of claim 1, wherein a vertical distance between the first pivot and a top end of the first vertical column is adjustable.

14. The surgical table of claim 1, wherein the first member comprises a longitudinally extending slot extending generally parallel to the longitudinal length of the first segment of the patient support, and the first pivot extends through the slot, the slot being displaceable along the first pivot.

15. The surgical table of claim 1, further comprising a drive system, which in causing the first segment and the second segment to articulate relative to each other about the joint, acts on first and second locations of the patient support, the first location being near the joint and the second location being on the first segment of the patient support between the first and second ends and spaced apart from the first location.

16. The surgical table of claim 15, wherein the second location is near the first end of the first segment of the patient support.

17. The surgical table of claim 15, wherein the first location is at the joint.

18. The surgical table of claim 15, wherein the drive system comprises an element extending along at least a portion of the first segment of the patient support between the first and second locations.

19. The surgical table of claim 18, wherein the element comprises a screw drive.

20. The surgical table of claim 18, wherein, in causing the first segment and the second segment to articulate relative to each other about the joint, the drive system further acts on a third location, the third location being on the second segment of the patient support.

21. The surgical table of claim 20, wherein the element comprises a cable and the joint comprises an extension extending from the joint against which the cable acts.

22. The surgical table of claim 1, further comprising a drive system configured to articulate the first segment and the second segment relative to each other about the joint, the drive system comprising an element operably coupled to the first segment and the second segment.

23. The surgical table of claim 22, wherein the element extends along at least a portion of the first segment of the patient support.

24. The surgical table of claim 23, wherein the element comprises a cable and the joint comprises an extension extending from the joint against which the cable acts.

25. The surgical table of claim 23, wherein the element comprises a screw drive.

26. The surgical table of claim 1, wherein the joint comprises a hinged arrangement between the second end of the first segment and third end of the second segment.

* * * * *